US010174382B2

(12) United States Patent
Buechler et al.

(10) Patent No.: US 10,174,382 B2
(45) Date of Patent: Jan. 8, 2019

(54) BREAST CANCER PROGNOSTICATION AND SCREENING KITS AND METHODS OF USING SAME

(71) Applicants: University of Notre Dame, Notre Dame, IN (US); Indiana University Research and Technology Corporation, Indianapolis, IN (US)

(72) Inventors: Steven Buechler, Granger, IN (US); Sunil Badve, Indianapolis, IN (US); Yesim Gokmen-Polar, Indianapolis, IN (US)

(73) Assignees: University of Notre Dame, Sound Bend, IN (US); Indiana University Research and Technology Corporation, Indianapolis, IN (US)

( * ) Notice: Subject to any disclaimer, the term of this patent is extended or adjusted under 35 U.S.C. 154(b) by 320 days.

(21) Appl. No.: 14/711,566

(22) Filed: May 13, 2015

(65) Prior Publication Data

US 2016/0333413 A1 Nov. 17, 2016

(51) Int. Cl.
*C12Q 1/68* (2018.01)
*C07H 21/04* (2006.01)
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
CPC ......... G01N 2800/52; G01N 33/57415; G01N 33/574; C12Q 1/6886; C12Q 2600/158; C12Q 2600/106; C12Q 2600/118; C12Q 2600/112
See application file for complete search history.

(56) References Cited

U.S. PATENT DOCUMENTS

| | | | | |
|---|---|---|---|---|
| 8,597,885 B2 * | 12/2013 | Buechler | ............ | C12Q 1/6886 435/4 |
| 2010/0196906 A1 * | 8/2010 | Buechler | ............ | C12Q 1/6886 435/6.14 |
| 2012/0071346 A1 * | 3/2012 | Sotiriou | ............ | G01N 33/574 506/9 |

OTHER PUBLICATIONS

Ahern, H. The Scientist 9(15):20 (Jul. 1995).*
Buechler, S. et al. Journal of Clinical Oncology 32(15 Suppl):11063 (May 20, 2014).*
Perou et al., Molecular portraits of human breast tumors, Letters to Nature, Aug. 17, 2000, pp. 747-752, vol. 406, Macmillian Magazines Ltd.
Wirapati et al., Meta-analysis of gene expression profiles in breast cancer: toward a unified understanding of breast cancer subtyping and prognosis signatures, Breast Cancer Research, Jul. 28, 2008, 11 Pages, vol. 10 Issue 4, BioMed Central Ltd.
Elston et al., Pathological prognostic factors in breast cancer. I. The value of histological grade in breast cancer: experience from a large study with long-term follow-up, Histopathology, 1991, pp. 403-410, vol. 19.
Daik et al., A Multigene Assay to Predict Recurrence of Tamoxifen-Treated, Node-Negative Breast Cancer, The New England Journal of Medicine, Dec. 30, 2004, pp. 2817-2826, vol. 351 Issue 27, Massachusetts Medical Society.
Van 'T Veer et al., Gene expression profiling predicts clinical outcome of breast cancer, Letters to Nature, Jan. 31, 2002, pp. 530-536, vol. 415, Macmillan Magazines Ltd.
Parker et al., Supervised Risk Predictor of Breast Cancer Based on Intrinsic Subtypes, Journal of Clinical Oncology, Mar. 10, 2009, pp. 1160-1167, vol. 27 Issue 8, American Society of Clinical Oncology.
Dowsett et al., Comparison of PAM50 Risk of Recurrence Score With Oncotype DX and IHC4 for Predicting Risk of Distant Recurrence After Endocrine Therapy, Journal of Clinical Oncology, Aug. 1, 2013, 13 Pages, vol. 31 Issue 22, American Society of Clinical Oncology.
Filipits et al., The PAM50 Risk-of-Recurrence Score Predicts Risk for Late Distant Recurrence after Endocrine Therapy in Postmenopausal Women with Endocrine-Responsive Early Breast Cancer, Clinical Cancer Research, Feb. 11, 2014, pp. 1298-1305, vol. 20 Issue 5, American Association for Cancer Research.
Gnant et al., Predicting distant recurrence in receptor-positive breast cancer patients with limited clinicopathological risk: using the PAM50 Risk of Recurrence score in 1478 postmenopausal patients of the ABCSG-8 trial treated with adjuvant endocrine therapy alone, Annals of Oncology, Dec. 16, 2013, pp. 339-345, vol. 25 Issue 2, Oxford University Press.
Jørgensen et al., PAM50 breast cancer intrinsic subtypes and effect of gemcitabine in advanced breast cancer patients, ACTA Oncologica, 2014, pp. 776-787, vol. 53, Informa Healthcare.
Prat et al., Research-Based PAM50 Subtype Predictor Identifies Higher Responses and Improved Survival Outcomes in HER2-Positive Breast Cancer in the NOAH Study, Clinical Cancer Research, Jan. 15, 2014, pp. 511-521, vol. 20 Issue 2, American Association for Cancer Research.
Steven Buechler, Low expression of a few genes indicates good prognosis in estrogen receptor positive breast cancer, BMC Cancer, Jul. 20, 2009, 16 Pages, vol. 9 Issue 243, BioMed Central Ltd.

(Continued)

*Primary Examiner* — Jeanine A Goldberg
(74) *Attorney, Agent, or Firm* — Denise L. Mayfield; Husch Blackwell LLP

(57) ABSTRACT

A genetic biomarker panel is provided for prognosing late onset ER+ breast cancer relapse, in a breast cancer survivor patient. Kits are also provided for measuring levels or the presence of an identified panel of genetic biomarkers. Methods are also provided for identifying a breast cancer survivor patient at a relatively high risk of suffering a breast cancer relapse within 8 years of diagnosis, and therefore suitable for treatment with an aggressive chemotherapeutic regimen. The method may also be used for identifying a breast cancer survivor patient not at high risk of suffering a breast cancer relapse within 8 years of diagnosis, and thus not suitable for treatment with an aggressive chemotherapeutic regimen. The genetic biomarker panel includes an oligonucleotide/ nucleic acid sequence specific for the following genes: MKI67, SPAG5, ESPL1, PLK1, or a genetic panel for MKI67, SPAG5, ESPL1, PLK1 and PGR.

5 Claims, 13 Drawing Sheets

(56) References Cited

OTHER PUBLICATIONS

Tang et al., Risk of Recurrence and Chemotherapy Benefit for Patients With Node-Negative, Estrogen Receptor-Positive Breast Cancer: Recurrence Score Alone and Integrated With Pathologic and Clinical Factors, Journal of Clinical Oncology, Nov. 20, 2011, pp. 4365-4372, vol. 29 Issue 33, American Society of Clinical Oncology.

Nielsen et al., A Comparison of PAM50 Intrinsic Subtyping with Immunohistochemistry and Clinical Prognostic Factors in Tamoxifen-Treated Estrogen Receptor-Positive Breast Cancer, Clinical Cancer Research, Sep. 13, 2010, pp. 5222-5232, vol. 16 Issue 21, American Association for Cancer Research.

Wu et al., A Model-Based Background Adjustment for Oligonucleotide Expression Arrays, Journal of the American Statistical Association, Dec. 2004, pp. 909-917, vol. 99 Issue 468, American Statistical Association.

Curtis et al., The genomic and transcriptomic architecture of 2,000 breast tumours reveals novel subgroups, Nature, 2012, 7 Pages, Macmillan Publishers Limited.

Fraley et al., Model-Based Clustering, Discriminant Analysis, and Density Estimation, Journal of the American Statistical Association, Jun. 2002, pp. 611-631, vol. 97 Issue 458, American Statistical Association.

Fraley et al., mclust Version 4 for R: Normal Mixture Modeling for Model-Based Clustering, Classification, and Density Estimation, Technical Report No. 597, Jun. 2012, 57 Pages, Department of Statistics, University of Washington, Seattle, Washington, USA.

Robert J. Gray, Flexible Methods for Analyzing Survival Data Using Splines, With Applications to Breast Cancer Prognosis, Journal of the American Statistical Association, Dec. 1992, pp. 942-951, vol. 87 Issue 420, American Statistical Association.

Paik et al., Gene Expression and Benefit of Chemotherapy in Women With Node-Negative, Estrogen Receptor-Positive Breast Cancer, Journal of Clinical Oncology, Aug. 10, 2006, pp. 3726-3734, vol. 24 Issue 23, American Society of Clinical Oncology.

Sotiriou et al., Gene Expression Profiling in Breast Cancer: Understanding the Molecular Basis of Histologic Grade to Improve Prognosis, Journal of the National Cancer Institute, Feb. 15, 2006, pp. 262-272, vol. 98 Issue 4, Oxford University Press.

Kelly et al., Agreement in Risk Prediction Between the 21-Gene Recurrence Score Assay (Oncotype DX®) and the PAM50 Breast Cancer Intrinsic Classifier™ in Early-Stage Estrogen Receptor-Positive Breast Cancer, The Oncologist, 2012, pp. 492-498, vol. 17, AlphaMed Press.

* cited by examiner

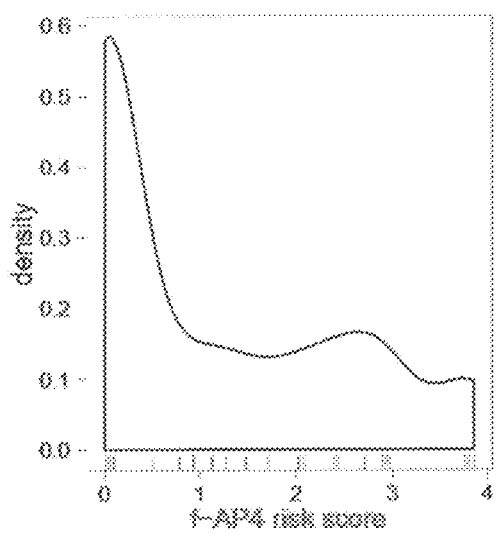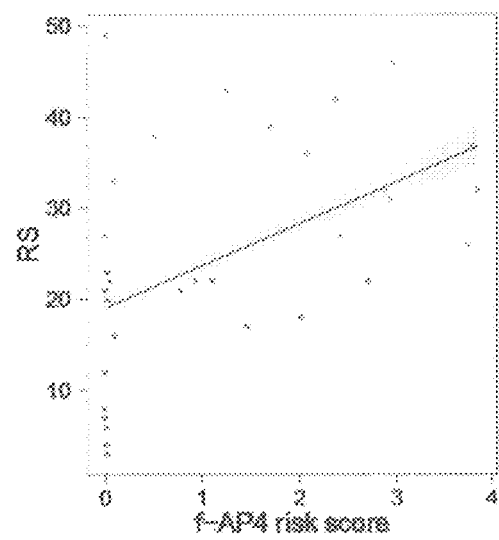

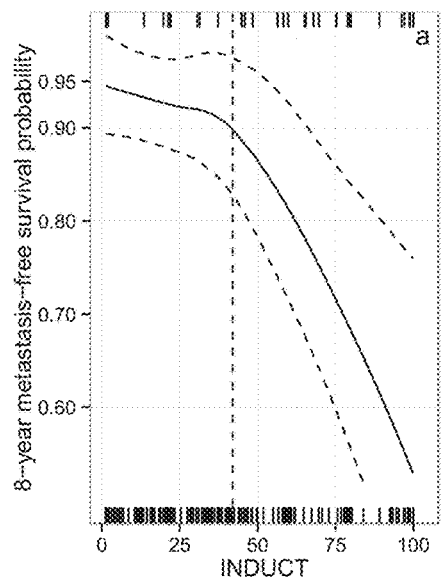
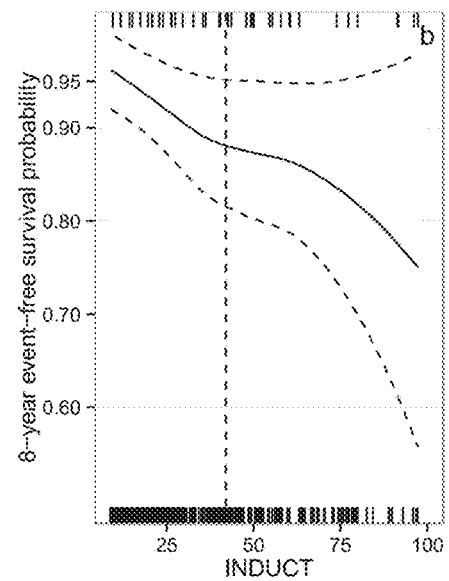
FIG. 10AFIG. 10B
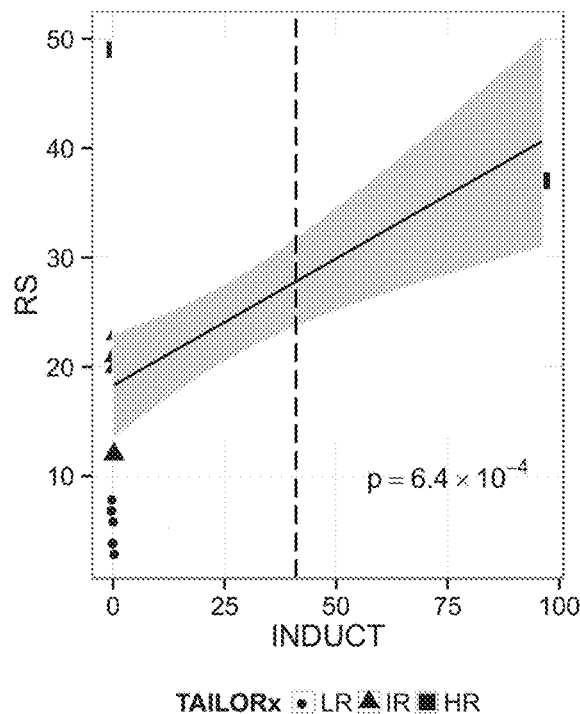
FIG. 11

BREAST CANCER PROGNOSTICATION AND SCREENING KITS AND METHODS OF USING SAME

STATEMENT REGARDING FEDERALLY SPONSORED RESEARCH OR DEVELOPMENT

This invention was made with government support under RR025761 awarded by the National Institutes of Health. The Government has certain rights in the invention.

FIELD OF THE INVENTION

The invention relates generally to the field of molecular genetic tests for breast cancer, as kits, molecular probes, and diagnostic/prognostic genetic tests for breast cancer are presented.

BACKGROUND OF THE INVENTION

One challenge of cancer treatment is targeting specific treatment regimens to pathogenically distinct tumor types, and ultimately personalizing tumor treatment to maximize outcome. For example, prognostication of breast cancer can be difficult as such patients may remain free of distant metastasis even without adjuvant chemotherapy. While standard clinical traits (or biomarkers) struggle to identify "good prognosis" patients with adequate precision, analyses of gene expression patterns through molecular biology in primary tumors have resulted in more successful diagnostic tests. These tests use continuous measurements of mRNA concentrations of numerous genes to determine a risk of metastasis in lymph node negative (LN) breast cancer patients with other clinical traits. The decision to use adjuvant chemotherapy to treat early-stage breast cancer must balance a reduced risk of recurrence with the adjuvant chemotherapy's toxic effects.

Such tests include the 21-gene screening panel, Oncotype DX® (Genomic Health—Redwood City, Calif.; see also, Paik (2004) *N. Engl. J. Med.* 351:2817-2826 and Paik (2006) *J. Clin. Oncol.* 24:3726-3734), the 70-gene array-based test Mammaprint® (Agendia—Amsterdam; see also, de Vijver (2002) *N. Engl. J. Med.* 347:1999-2009 and Buyse (2006) *J. Natl. Cancer Inst.* 98:1183-1192) and Prosigna. These tests apply to lymph node-negative tumors with various other clinical traits, and utilize continuous measurements of mRNA concentrations of numerous genes.

An accelerated progression (AP) relapse test was described for assessing the relative prognostic value of a cancer treatment for a patient having been diagnosed with breast cancer (U.S. Pat. No. 8,597,885; and Buechler (2009) *BMC* Cancer 9:243).

A need continues to exist for alternative prognostication tests that provide predictive information about a recovering breast cancer patient's anticipated and/or likely probability for long-term survival. While the Oncotype DX, Mammaprint® and Prosigna assays provide assessment of the likelihood of recurrence of early-stage, estrogen receptor-positive (ER+) breast cancer, among other things, they do not outperform traditional parameters (such as tumor size, grade and patient age). Hence, additional screening and/or selection techniques are needed in the medical arts to advance and improve individual informed treatment decisions that can made for the breast cancer patient.

SUMMARY OF THE INVENTION

In a general and overall sense, the present invention provides improved and more accurate screening and prognostic tests and screening panels, for identifying human female breast cancer patients at a higher risk of breast cancer relapse within 8 years of initial breast cancer diagnosis.

In some aspects, a molecular-based kit and method of using the kit are disclosed for assessing a relative prognostic value of late ER+, LN– breast cancer recurrence, relapse-free survival probability up to 8 years following diagnosis, and/or effectiveness of a cancer treatment for a specific ER+, LN–, human female breast cancer patient. In some embodiments, the patient is an estrogen-receptor positive (ER+), lymph node negative (LN–) human female breast cancer patient.

In other embodiments, the invention provides a kit comprising a plurality of molecular probes, where each of the probes specifically binds to one distinct biomarker, fragment or variant thereof, and where the relative levels of the genes identified using the biomarkers correlate with the relative risk or probability of a breast cancer relapse or recurrence in a human female having had ER+, LN–, breast cancer. The probes can be nucleic acid probes or primers. The biomarkers to which the probes bind can be multi-state genes and can be a combination of MKI67, SPAG5, ESPL1, PLK1 and PGR.

In some aspects, the present invention provides a method for identifying an ER+ breast cancer patient at risk of relapse, where the patient being identified as having a relatively higher risk of relapse will be advised to consider receiving an aggressive anti-cancer therapeutic regimen so as to potentially avoid and/or reduce the probably onset of a relapse. In some embodiments, the method comprises obtaining a breast tissue specimen from the ER+ breast cancer patient so as to provide a patient test sample, measuring a level of each of a panel of genetic biomarkers in the patient test sample, the panel of genetic biomarkers consisting essentially of at least three of genes selected from the group consisting of: ESPL1, MKI67, SPAG5, PLK1 and PGR; normalizing the level of the genes measured in the patient sample against the levels of a control group of endogenous genes to provide a set of normalized patient gene levels of the selected genetic biomarkers, calculating a gene risk score between 0 and 1 for each of the set of normalized patient gene levels of the selected genetic biomarkers, computing a cumulative cancer test score between 0 to 100 for the gene risk score values identified for each genetic biomarker level obtained for the patient test sample, and administering an aggressive anti-cancer therapeutic regimen to an ER+ breast cancer patient having a cumulative cancer test score at least within an about $60^{th}$ percentile or higher of a reference heterogeneous ER+ breast cancer population. Alternatively, the ER+ breast cancer patient not demonstrating a cumulative cancer test score at least within an about 60 percentile or higher of a reference heterogeneous ER+ breast cancer population would be advised not to, or at least not receive a recommendation to, receive an aggressive anti-cancer therapeutic regimen.

The inclusion of a step for normalizing a patient sample gene measurement score against common endogenous genes decreases the genetic "noise" from nonspecific gene expression, thus enhancing the detectability of patient variation in the screening protocol. In addition, and because the normalized gene expression values for a reference population of patients range continuously from low values to high values with a large number of samples with values at a moderate level, and there are more relapse cases with high expression levels than low expression levels, and many more with moderate values that are as close to low (good prognosis) values as high (poor prognosis) values, additional steps are provided as part of the claimed protocols and screening techniques to reduce this uncertainty, or incidence of non-conclusive reading results, in patient sample readings.

Specifically, and in some embodiments of the methods/screening techniques, a gene risk score is determined for each gene/biomarker measured in the panel. In this process, a gene risk score is associated with each gene from 0 to 1, such that the gene risk scores increases along with the expression value of a gene/biomarker. A high risk patient sample would therefore have a gene risk score near 1, while a low risk patient sample would have a risk scores near 0. Using this technique, there are very few samples (<10%) with values between 0.25 and 0.75, and very few patient samples with a moderate risk score. Thus, the use of risk scores, rather than expression values, in calculating a final test score minimizes the number of samples who receive a test score with an unclear prognosis. Thus, the precision and specificity of the screening and prognostic methods described here are significantly improved. Use of the risk scores also reduces the test's standard error, and increases the reliability of the test. As an even further improvement, the present screening and prognostic methods include yet another analysis to improve accuracy and precision in the use of a cancer test score to be identified for each patient. In this step, a cancer test score is calculated for each ER+ breast cancer patient, this cancer test score being a value of 1 to 100. This patient value, when compared to the values obtained from a heterogeneous population of ER+ breast cancer patients in a given population, is demonstrated by the present inventors to provide yet an additional added measure of predictive value of risk for cancer relapse to the present screening methods. Specifically, it was found that a patient having a cumulative cancer test score (determined according the methods described herein) that fell within an about 60 percentile (or $65^{th}$, $70^{th}$, $80^{th}$, or $60^{th}$ to $90^{th}$ percentile) or higher of a reference cumulative average cancer test scores from a heterogeneous ER+ breast cancer population, could more reliably be identified as a patient at relatively much higher risk of relapse. Conversely, it was found that a patient having a cumulative cancer test score (determined according to the methods described herein) that did not fall within an about $60^{th}$ percentile (or $65^{th}$, $70^{th}$, $80^{th}$, or $60^{th}$ to $90^{th}$ percentile) or higher of the reference cumulative average cancer test scores from a heterologous ER+ breast cancer population, could more reliably be identified as a patient at a relatively much lower risk of relapse. The lower range of the percentile may also be described as the lower $20^{th}$, $30^{th}$, $40^{th}$, $50^{th}$, or less than $60^{th}$ percentile, of the reference cumulative average cancer test scores from a heterologous ER+ breast cancer population, and is correlated with relatively low risk cancer relapse ER+ patients.

The intricate and overlapping nature of the specific approach taken by the presently described screening and prognostic methods therefore provides a test with a much greater level of certainty as relates to an individual patient result, having a much smaller, or even nonexistent, group of patients left without a reliable indicator of risk or direction concerning recommended future treatment.

In other embodiments, the methods include a step of measuring the level of nucleic acid transcripts of a defined set of biomarkers in a breast tissue sample from a ER+, LN− breast cancer human female patient. In some embodiments, the biomarkers can be a combination of the biomarkers as described herein. The methods also include correlating expression levels via an algorithm to determine whether the patient has a good/favorable prognosis or a bad/poor prognosis for the recurrence of an ER+, LN− cancer.

Expression levels can be measured by, for example, nucleic acid hybridization or quantitative reverse transcription polymerase chain reaction ("RT-PCR"). Likewise, expression levels can be correlated or normalized to expression levels of a control or reference set by, for example, an accelerated progression (AP) relapse test. During the correlating or normalizing, a continuous risk score can be used to measure probability of membership in a component. In this way, the continuous risk score can be used to measure probability that the patient is low-risk for relapse with a good/favorable prognosis or high-risk for relapse with a bad/poor prognosis. Patients overexpressing at least one, or at least two, of MK167, SPAG5, ESPL1, PLK1 and underexpressing PGR, tend to have a bad/poor prognosis, thus these biomarkers are predictive of a high risk of relapse.

The methods also can include developing an appropriate treatment option(s) for the patient depending upon whether the patient's prognosis is good/favorable or bad/poor.

The kits and methods therefore find use in prognostication assays that can simultaneously provide predictive information about a breast cancer patient's likelihood of relapse and/or response to a variety of treatment options.

These and other advantages, effects, features and objects of the invention will become better understood from the description that follows.

In the description, reference is made to the accompanying drawings, which form a part hereof and in which there is shown by way of illustration, not limitation, embodiments of the invention.

The following abbreviations are used throughout the present application:

BLAST (Basic Local Alignment Search Tool)
Confidence interval (CI)
Cox proportional hazard (CPH)
Estrogen receptor (ER)
Formalin-fixed, paraffin-embedded (FFPE)
Genomic Grade Index (GGI)
High risk (HR)
Indiana Notre Dame Universities' Clinical Translational (INDUCT)
Intermediate risk (IR)
Low risk (LR)
Lymph node (LN)
Real-time quantitative-real time polymerase chain reaction (qrt-PCR)
Recurrence score (RS)
Recurrence score including clinical parameters (RSCP)
Reference sequence (REFSEQ)

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 1A shows the four vectors that are added to form the AP4 risk score all have values ranging from 0 to 1, with the majority near 0. The AP4 risk score clusters many values near 0, predicting a low risk of metastasis. On the other hand, a score near 4 means that the patient was in the poor prognosis component of all 4 genes. Correspondingly, a high percentage of these patients metastasize. FIG. 1B shows the expected probability of metastasis for a given value s of the AP4 risk score was estimated using subsets of the sample space with AP4 risk scores spanning an interval around s. The probability of metastasis is near 0.1 until the score nears 2.

FIG. 6A-FIG. 6B show f-AP4 risk score in the validation set of FFPE samples with FIG. 6A f-AP4 density distribution with TAILORx risk groups, and FIG. 6B f-AP4 versus Recurrence Score. FIG. 6A, as the colored hash marks show, the percentage of high risk samples increases with the f-AP4 risk score. The manner in which f-AP4 is defined produces many points with scores near 0. FIG. 6B shows a linear fit of the recurrence score against the f-AP4 has a p-value of 0.0017 and an adjusted R2=0.23. The low value of the adjusted R2 reflects the fact that many samples with varying RS values have an f-AP4 score near 0.

FIG. 10A-FIG. 10B. Eight-year expected survival as a function of the INDUCT score is plotted for the LN− Tamoxifen treated samples in FIG. 10A the Affymetrix validation sets and FIG. 10B the Metabric validation set. The Cox-spline method [12] was used to fit these curves. The dashed lines represent the 95% confidence interval. The actual INDUCT values colored by event status are plotted at the bottom of the figures. The dotted vertical line at the value 42 indicates the threshold for creating the discrete INDUCT score. A Cox proportional hazard model using INDUCT as its only variable has a P-value $1.4 \times 10^{-9}$ in the Affymetrix set and 0.003 in Metabric. Score values for relapse cases are plotted on the top edge while score values for the non-relapse cases are plotted on the bottom edge.

FIG. 11. The INDUCT score versus RS is plotted in the validation set of FFPE samples. A linear fit of the RS against INDUCT has a P value of $6.4 \times 10^4$ and an adjusted $R^2=0.27$. The low value of the adjusted $R^2$ reflects the fact that many samples with varying RS values have an INDUCT score near 0. The vertical line at INDUCT=42 divides the samples into INDUCT low risk and INDUCT high risk groups. There is significance dependence between the INDUCT binary risk classification and the TAILORx risk groups (P=0.004) and the oncotype DX risk groups (P=0.03).

Figure 1A:
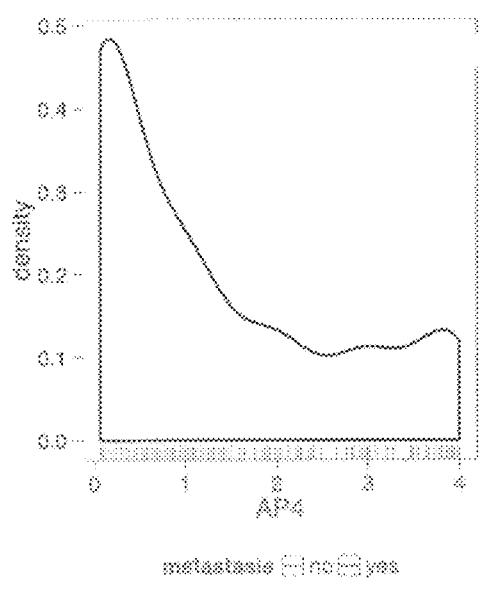
FIG. 1A-FIG. 1B. show risk score characteristics in microarray data with FIG. 1A density distribution, and FIG. 1B probability of metastasis within eight years.
Figure 1B:
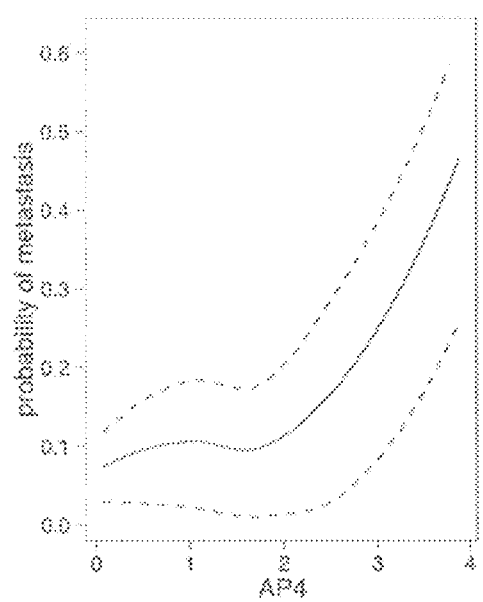
Figure 2:
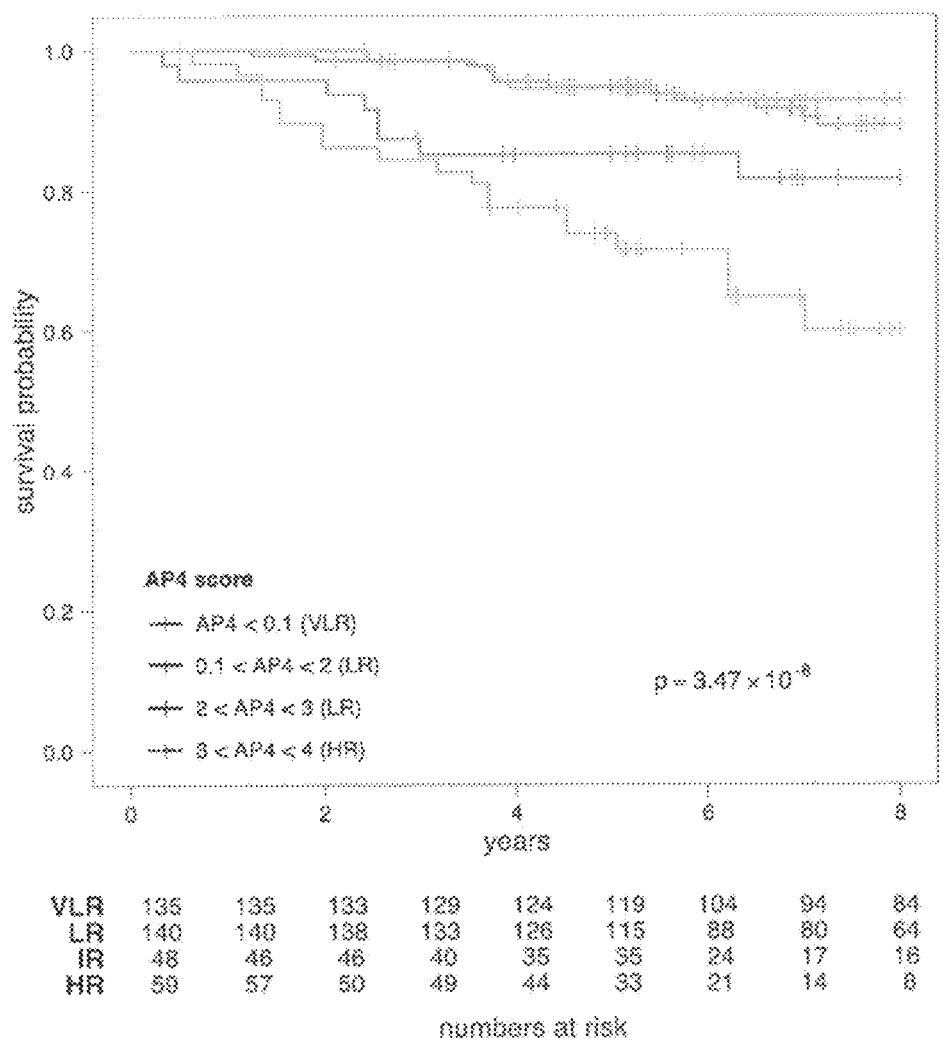
FIG. 2. shows a Kaplan-Meier plot for AP4 strata in the microarray dataset. The strata were defined using natural boundaries in the AP4 risk score. The expected survival probability if the lowest two strata are nearly identical for six years.
Figure 3:
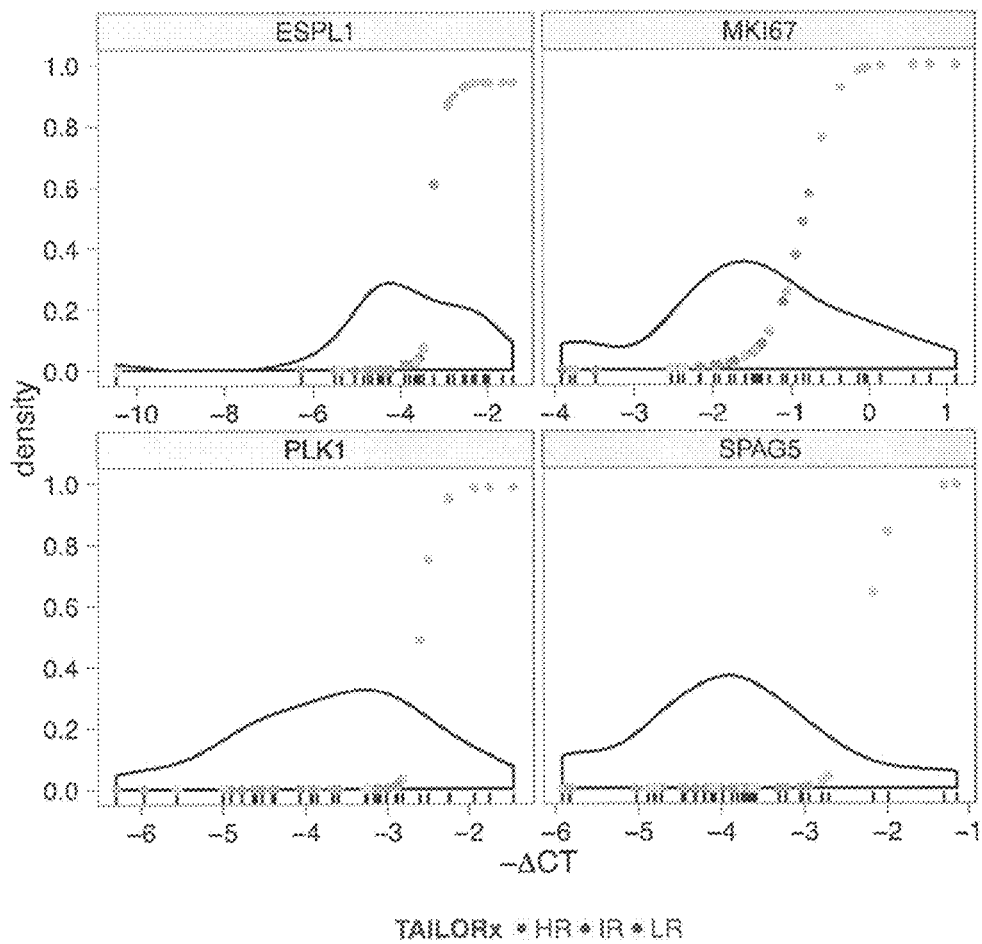
FIG. 3. shows density distribution of expression values in the training set of formalin fixed, paraffin-embedded (FFPE) samples for four genes, ESPL-1, MKI67, PLK1 and SPAG5. The points are values of the risk score calculated from components of the mixture model fit. The points are marked by the TAILORx risk category, showing that for each of these genes nearly all of the points in the high component are in the high risk category.
Figure 4:
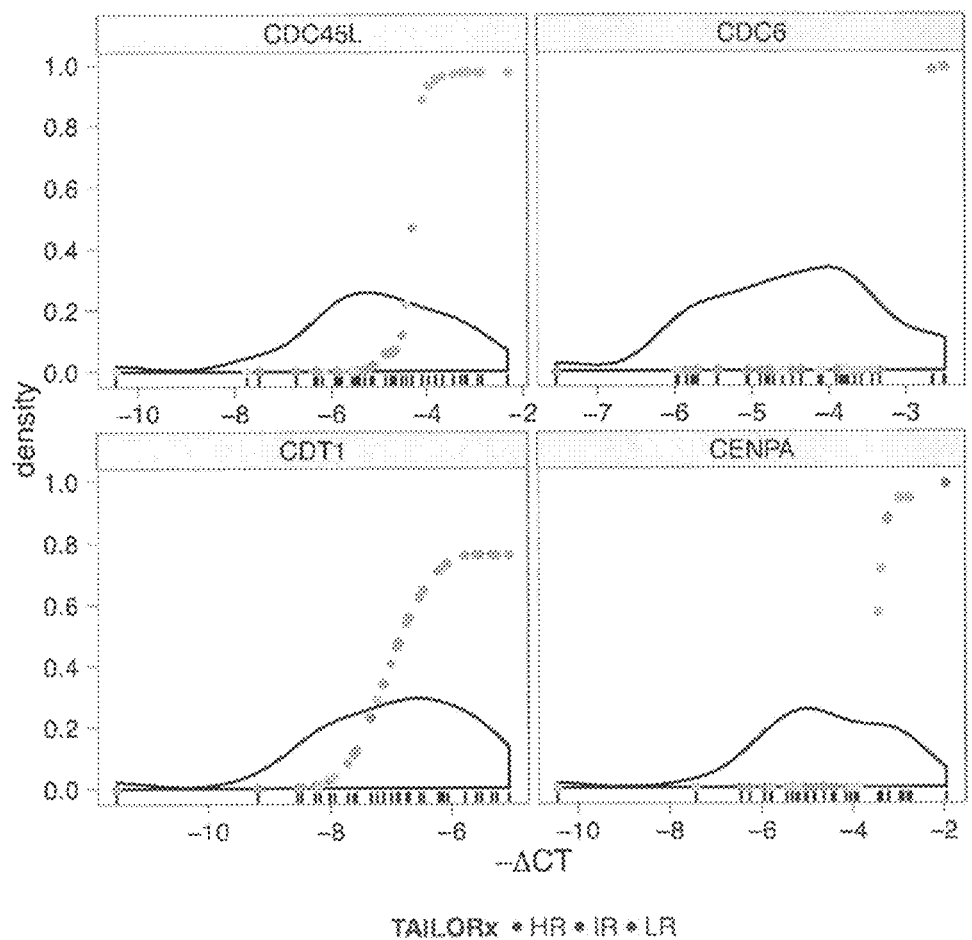
FIG. 4. shows a density distribution of expression values in the training set of FFPE samples for four genes, CDC45L, CDC6, CDT1 and CENPA.
Figure 5:
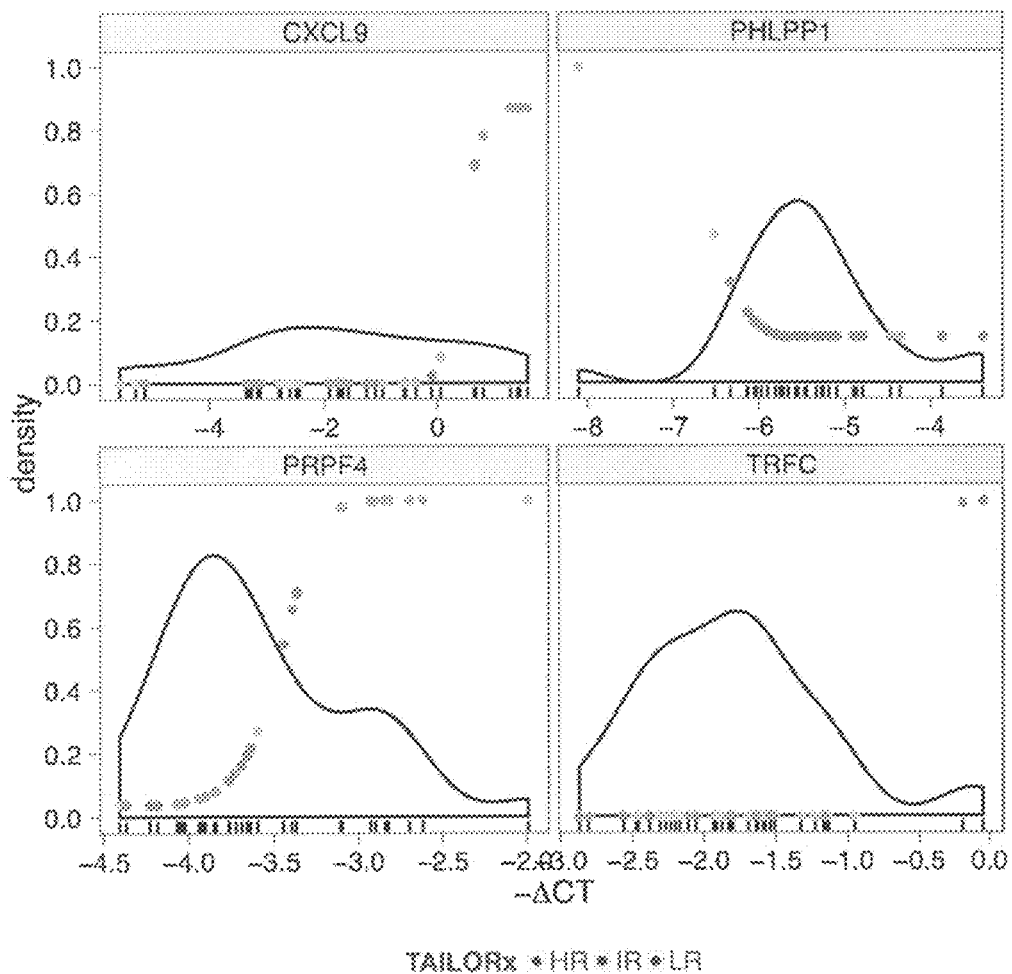
FIG. 5. shows a density distribution of expression values in the training set of FFPE samples for four genes, CXCL9, PHLPP1, PRPF4 and TRFC.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The biomarkers, kits and methods now will be described more fully hereinafter with reference to the accompanying drawings, in which some, but not all embodiments of the invention are shown. The invention may be embodied in many different forms and should not be construed as limited to the embodiments set forth herein; rather, these embodiments are provided so that this disclosure will satisfy applicable legal requirements.

Likewise, many modifications and other embodiments of the kits and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "patient" means an individual having symptoms of, or at risk for, cancer or other malignancy. A patient may be human or non-human and may include, for example, animal strains or species used as "model systems" for research purposes, such a mouse model. Likewise, patient may include either adults or juveniles (e.g., children). Moreover, patient may mean any living organism, preferably a mammal (e.g., human or non-human) that may benefit from the administration of compositions contemplated herein.

As used herein, "prognose," "prognosing," "prognosticating" and the like mean predictions about or predicting a likely course or outcome of a disease or disease progression, particularly with respect to a likelihood of, for example, disease remission, disease relapse, disease progression including tumor recurrence, metastasis and cancer-attributable death (i.e., the outlook for chances of survival), as well as drug resistance of a neoplastic disease, As used herein, "good prognosis" or "favorable prognosis" means a likelihood that a patient having cancer, particularly breast cancer, will remain disease-free (i.e., cancer-free). As used herein, "poor prognosis" or "bad prognosis" means a likelihood of a relapse or recurrence of the underlying cancer or tumor, metastasis or death. As such, patients classified as having a good prognosis tend to remain free of the underlying cancer or tumor. Conversely, patients classified as having a bad prognosis tend to experience disease relapse, tumor recurrence, metastasis or death.

Relatedly, "prediction" means a likelihood that a patient will respond favorably or unfavorably to a therapeutic or therapeutic combination, and also the extent of those responses, or that a patient will survive, following surgical removal of a primary tumor and/or chemotherapy for a certain period of time, without a significant risk of cancer recurrence. The predictive methods described herein can be used clinically to make treatment decisions by facilitating the most appropriate treatment modalities for an individual patient based on molecular genetic factors. They also can be valuable tools in predicting if a patient is likely to respond favorably to a treatment regimen, such as surgical intervention, chemotherapy with a given therapeutic or therapeutic combination, and/or radiation therapy, or whether long-term survival of the patient, following surgery and/or termination of chemotherapy or other treatment modalities is likely.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "tumor" means neoplastic cell growth and proliferation, whether malignant or benign, and all pre-cancerous and cancerous cells and tissues.

As used herein, "cancer" and "cancerous" mean a physiological condition in mammals that typically is characterized by unregulated cell growth. Examples of cancer include, but are not limited to, bladder cancer, brain cancer, breast cancer, cervical cancer, colon cancer, gastric cancer, hepatocellular cancer, liver cancer, lung cancer, ovarian cancer, prostate cancer, pancreatic cancer, cancer of the urinary tract, thyroid cancer, renal cancer, carcinoma and melanoma. Of particular interest herein is breast cancer.

The work described herein is the first to show that a combination of MK167, SPAG5, ESPL1 and PLK1 can be used as biomarkers in breast cancer prognostication, where a patient having an overexpression of at least one of these biomarkers tends to have a bad/poor prognosis, and thus predictive and high risk of relapse. As used herein, "biomarker" or "biomarkers" means nucleic acid (e.g., gene) or amino acid (e.g., protein) molecules whose level of expression in a cell, tissue, organ or mammal is altered compared to that of a normal or healthy cell, tissue, organ or mammal.

Moreover, biomarkers can be multi-state within a patient population and have expression levels that correlate with, for example, a cancer, particularly breast cancer, and prognosis thereof. As used herein, "multi-state gene" and the like means a biomarker, such as a gene, that is capable of differential levels of expression within a patient population such that the expression levels of the biomarker in the patient population permits the patient population to be divided into at least two or more distribution groups based on density distribution according to statistical analysis of the expression level. For example, expression levels can be divided into two groups based on a mixture model fit of expression levels of the biomarker of interest.

The biomarkers can include polynucleotides comprising the entire or partial sequence of the nucleotide sequence encoding the biomarkers, or the complement of such sequences. As used herein, "polynucleotide" means a polymer of nucleic acids or nucleotides that, unless otherwise limited, encompasses naturally occurring bases (i.e., adenine, guanine, cytosine, thymine and uracil) or known base analogues having the essential nature of naturally occurring nucleotides in that they hybridize to single-stranded nucleic acid molecules in a manner similar to naturally occurring nucleotides. Although it may comprise any type of nucleotide units, the term generally applies to nucleic acid polymers of ribonucleotides ("RNA") or deoxyribonucleotides ("DNA"). The term includes single-stranded nucleic acid polymers, double-stranded nucleic acid polymers, and RNA and DNA made from nucleotide or nucleoside analogues that can be identified by their nucleic acid sequences, which are generally presented in the 5' to 3' direction (as the coding strand), where the 5' and 3' indicate the linkages formed between the 5' hydroxyl group of one nucleotide and the 3'-hydroxyl group of the next nucleotide. For a coding strand presented in the 5'-3' direction, its complement (or non-coding strand) is the strand that hybridizes to that sequence according to Watson-Crick base pairing. Thus, as used herein, the complement of a nucleic acid is the same as the "reverse complement" and describes the nucleic acid that in its natural form, would be based paired with the nucleic acid in question.

As used herein, a "nucleic acid," "nucleotide" or "nucleic acid residue" are used interchangeably to mean a nucleic acid that is incorporated into a molecule such as a gene or other polynucleotide. As noted above, the nucleic acid may be a naturally occurring nucleic acid and, unless otherwise limited, may encompass known analogues of natural nucleic acids that can function in a similar manner as naturally occurring nucleic acids. Examples of nucleic acids include any of the known base analogues of DNA and RNA such as, but not limited to, 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As such, the biomarkers can include DNA or RNA comprising the entire or partial nucleotide sequence thereof. It is contemplated that in some instances, the amino acid sequences of the biomarkers can be used.

The biomarkers can include not only the entire biomarker sequence but also fragments and/or variants thereof. As used herein, "fragment" or "fragments" means a portion of the nucleic or amino acid sequence of the biomarker. Polynucleotides that are fragments of a biomarker nucleic acid sequence generally comprise at least about 10, 15, 20, 50, 75, 100, 150, 200, 250, 300, 350, 400, 450, 500, 550, 600, 650, 700, 800, 900, 1,000, 1,200 or 1,500 contiguous nucleotides, or up to the number of nucleotides present in a full-length biomarker polynucleotide disclosed herein. Likewise, a fragment of a biomarker polypeptide comprises at least about 15, 25, 30, 50, 100, 150, 200 or 250 contiguous amino acids, or up to the total number of amino acids present in a full-length biomarker protein.

As used herein, "variant" or "variants" means substantially similar sequences. Generally, variants of a particular biomarker have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity (preferably over the full length) to a biomarker as determined by sequence alignment programs.

One of skill in the art understands that variants can be constructed via modifications to either the polynucleotide or polypeptide sequence of the biomarker and can include substitutions, insertions (e.g., adding no more than ten nucleotides or amino acid) and deletions (e.g., deleting no more than ten nucleotides or amino acids). Methods of mutating and altering nucleic acid sequences, as well as DNA shuffling, are well known in the art. See, e.g., Crameri et al. (1997) *Nature Biotech.* 15:436-438; Crameri et al. (1998) *Nature* 391:288-291; Kunkel (1985) *Proc. Natl. Acad Sci. USA* 82:488-492; Kunkel et al. (1987) *Methods in Enzymol.* 154:367-382; Moore et al. (1997) *J. Mol. Biol.* 272:336-347; Stemmer (1994) *Proc. Natl. Acad Sci. USA* 91:10747-10751; Stemmer (1994) *Nature* 370:389-391; Zhang et al. (1997) *Proc. Natl. Acad Sci. USA* 94:4504-4509; and *Techniques in Molecular Biology* (Walker & Gaastra eds., MacMillan Publishing Co. 1983) and the references cited therein; as well as U.S. Pat. Nos. 4,873,192; 5,605,793 and 5,837,458.

Methods of aligning sequences for comparison are well known in the art. Thus, the determination of percent sequence identity between any two sequences can be accomplished using a mathematical algorithm. Non-limiting examples of such mathematical algorithms are the algorithm of Myers & Miller (1988) *CAB/OS* 4:11-17; the local alignment algorithm of Smith et al. (1981) *Adv. Appl. Math.* 2:482; the global alignment algorithm of Needleman & Wunsch (1970) *J. Mol. Biol.* 48:443-453; the search-for-local alignment method of Pearson & Lipman (1988) *Proc. Natl. Acad. Sci. USA* 85:2444-2448; the algorithm of Karlin & Altschul (1990) *Proc. Natl. Acad Sci. USA* 87:2264, modified as in Karlin & Altschul (1993) *Proc. Natl. Acad Sci. USA* 90:5873-5877.

As noted above, biomarkers for use in the kits and methods described herein include biomarkers that provide a specific indication that ESPL1, MK167, SPAG5, PLK1 and/or PGR.

Nucleic and amino acid sequences for MK167 are known and characterized, see, e.g., GenBank® Accession No. NM_002417.

Nucleic and amino acid sequences for SPAG5 are known and characterized, see, e.g., GenBank® Accession No. NM_006461.

Nucleic and amino acid sequences for ESPL1 are known and characterized, see, e.g., GenBank® Accession No. NM_012291.

Nucleic and amino acid sequences for PLK1 are known and characterized, see, e.g., GenBank@ Accession No. NM_005030.

Nucleic and amino acid sequences for PGR are known and characterized, see, e.g., GenBank® Accession No. 000926.

Based upon the work described herein, kits and methods for breast cancer prognostication are described that are based upon probes to MKI67, SPAG5 ESPL1, PLK1 and/or PGR. Specifically, probes 212022_s_at (MKI67), 203145_at (SPAG5), 204817_at (ESPL 1), 202240_at (PLK1), and 208305_at (PGR) were used.

Kits

Compositions of the invention can include kits for prognosing an individual having or suspected of having cancer, particularly an individual having or suspected of having breast cancer. As used herein, "kit" or "kits" means any manufacture (e.g., a package or a container) including at least one reagent, such as a nucleic acid probe or the like, for specifically detecting the expression of the biomarkers described herein. As used herein, "probe" means any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies and organic molecules. The kit will, in some embodiments, include an instructional insert, or contain instructions for use on a label or other surface available for print on the product.

When making polynucleotides for use as probes to the biomarkers (e.g., hybridization probes or primer sets), one of skill in the art can be further guided by knowledge of redundancy in the genetic code as shown below in Table 1.

TABLE 1

Redundancy in Genetic Code.

| Residue | Triplet Codons Encoding the Residue |
|---|---|
| Ala (A) | GCU, GCC, GCA, GCG |
| Arg (R) | CGU, CGC, CGA, CGG, AGA, AGG |
| Asn (N) | AAU, AAC |
| Asp (D) | GAU, GAC |
| Cys (C) | UGU, UGC |
| Gln (Q) | CAA, CAG |
| Glu (E) | GAA, GAG |
| Gly (G) | GGU, GGC, GGA, GGG |
| His (H) | CAU, CAC |
| Ile (I) | AUU, AUC, AUA |
| Leu (L) | UUA, UUG, CUU, CUC, CUA, CUG |
| Lys (K) | AAA, AAG |
| Met (M) | AUG |
| Phe (F) | UUU, UUC |
| Pro (P) | CCU, CCC, CCA, CCG |
| Ser (S) | UCU, UCC, UCA, UCG, AGU, AGC |
| Thr (T) | ACU, ACC, ACA, ACG |
| Trp (W) | UGG |
| Tyr (Y) | UAU, UAC |
| Val (V) | GUU, GUC, GUA, GUG |
| START | AUG |
| STOP | UAG, UGA, UAA |

Methods of synthesizing polynucleotides are well known in the art, such as cloning and digestion of the appropriate sequences, as well as direct chemical synthesis (e.g., ink-jet deposition and electrochemical synthesis). Methods of cloning polynucleotides are described, for example, in Copeland et al. (2001) *Nat. Rev. Genet.* 2:769-779; *Current Protocols in Molecular Biology* (Ausubel et al. eds., John Wiley & Sons 1995); *Molecular Cloning: A Laboratory Manual*, 3rd ed. (Sambrook & Russell eds., Cold Spring Harbor Press 2001); and *PCR Cloning Protocols,* 2nd ed. (Chen & Janes eds., Humana Press 2002). Methods of direct chemical synthesis of polynucleotides include, but are not limited to, the phosphotriester methods of Reese (1978) *Tetrahedron* 34:3143-3179 and Narang et al. (1979) *Methods Enzymol.* 68:90-98; the phosphodiester method of Brown et al. (1979) *Methods Enzymol.* 68:109-151; the diethylphosphoramidate method of Beaucage et al. (1981) *Tetrahedron Lett.* 22:1859-1862; and the solid support methods of Fodor et al. (1991) *Science* 251:767-773; Pease et al. (1994) *Proc. Natl. Acad Sci. USA* 91:5022-5026; and Singh-Gasson et al. (1999) *Nature Biotechnol.* 17:974-978; as well as U.S. Pat. No. 4,485,066. See also, Peattie (1979) *Proc. Natl. Acad Sci. USA* 76:1760-1764; as well as EP Patent No. 1721908; Int'l Patent Application Publication Nos. WO 2004/022770 and WO 2005/082923; US Patent Application Publication Nos. 2009/0062521 and 2011/0092685; and U.S. Pat. Nos. 6,521,427; 6,818,395; 7,521,178 and 7,910,726.

The kits can be promoted, distributed or sold as units for performing the methods described below. Additionally, the kits can contain a package insert describing the kit and methods for its use. For example, the insert can include instructions for correlating the level of biomarker expression measured with a patient's likelihood of cancer recurrence, long-term survival, and the like, and select the most appropriate treatment option accordingly.

The kits therefore can be used for prognosing a breast cancer with biomarkers at the nucleic acid level. Such kits are compatible with both manual and automated nucleic acid detection techniques (e.g., gene arrays, Northern blotting or Southern blotting). These kits can include a plurality of probes, for example, from 2 to 30 nucleic acid probes that specifically bind to distinct biomarkers, fragments or variants thereof. Alternatively, the kits can contain at least 2 probes, at least 3 probes, at least 4 probes, at least 5 probes, at least 6 probes, at least 7 probes, at least 8 probes, at least 9 probes, at least 10 probes, at least 11 probes, at least 12 probes, at least 13 probes, at least 14 probes, at least 15 probes, at least 16 probes, at least 17 probes, at least 18 probes, at least 19 probes, or at least 20 probes. For example, the kits described herein used 4 probes including 212022_s_at (MKI67), 203145_at (SPAG5), 204817_at (ESPL1), 202240_at (PLK1), or 5 probes including 212022_s_at (MKI67), 203145_at (SPAG5), 204817_at (ESPL1), 202240_at (PLK1), and 208305_at (PGR).

Any or all of the kit reagents can be provided within containers that protect them from the external environment, such as in sealed containers. Positive and/or negative controls can be included in the kits to validate the activity and correct usage of reagents employed in accordance with the invention. Controls can include samples, such as tissue sections, cells fixed on glass slides, RNA preparations from tissues or cell lines, and the like, known to be either positive or negative for the presence of at least five different biomarkers. The design and use of controls is standard and well within the routine capabilities of one of skill in the art.

Methods

Methods of the invention include prognosing a patient having an ER+ breast cancer for risk of relapse with or without subsequent treatment. The method can include determining the expression levels of RNA transcripts or expression products thereof of at pre-selected number of biomarkers in a sample from the individual. The methods also can include comparing the expression level of the biomarkers to a reference or reference set of expression levels from a cohort of, for example, ER+ breast cancer patients to determine whether the expression level of each gene is low or high in comparison to the reference set and then creating a report summarizing the data, where the patient is given a prognosis of an increased likelihood of long-term survival without breast cancer recurrence if the expression level of at least one of the biomarkers is low or where the patient is given a prognosis of a decreased likelihood of long-term survival with breast cancer recurrence or metastasis and a prescription for chemotherapy if the expression level of at least one of the biomarkers is high.

One of skill in the art is familiar with the time frame(s) for assessing prognosis and outcome. Examples of such time frames include, but are not limited to, less than 1 year, about 1, 2, 3, 4, 5, 6, 7, 8, 9 or 10 years or more years. With respect to breast cancer, the relevant time for assessing prognosis or disease-free survival time often begins with the surgical removal of the tumor or suppression, mitigation or inhibition of tumor growth. Thus, for example, a good prognosis can be a likelihood that the individual having breast cancer will remain free of the underlying cancer or tumor for a period of at least about 5, more particularly, a period of at least about 8-10 years. In contrast, for example, a bad prognosis can be a likelihood that the individual having ER+ breast cancer will experience disease relapse, tumor recurrence, metastasis or death within a period of less than about 3 years, less than about 5 years, more particularly a period of less than about 8 years.

The methods generally begin by collecting a sample from a patient pre-determined to have cancer. As used herein "sample" means any collection of cells, tissues, organs or bodily fluids in which expression of a biomarker can be detected. Examples of such samples include, but are not limited to, biopsy specimens of cells, tissues or organs, bodily fluids and smears.

When the sample is a biopsy specimen, it can include, but is not limited to, breast cells, particularly breast tissue from a biopsy, such as a breast tumor tissue sample. Biopsy specimens can be obtained by a variety of techniques including, but not limited to, scraping or swabbing an area, using a needle to aspirate cells or bodily fluids, or removing a tissue sample. Methods for collecting various body samples/biopsy specimens are well known in the art. In some embodiments, a breast tissue sample is obtained by, for example, fine needle aspiration biopsy, core needle biopsy, or excisional biopsy.

Fixative and staining solutions can be applied to, for example, cells or tissues for preserving them and for facilitating examination. Body samples, particularly breast tissue samples, can be transferred to a glass slide for viewing under magnification. For example, the body sample can be a FFPE breast tissue sample, particularly a primary breast cancer sample.

After collecting and preparing the specimen from the patient, the methods then include detecting expression of the biomarkers. One can use any method available for detecting expression of polynucleotide and polypeptide biomarkers. As used herein, "detecting expression" means determining the quantity or presence of a biomarker polynucleotide or its expression product. As such, detecting expression encompasses instances where a biomarker is determined not to be expressed, not to be detectably expressed, expressed at a low level, expressed at a normal level, or overexpressed.

Expression of a biomarker can be determined by normalizing the level of a reference marker/control, which can be all measured transcripts (or their products) in the sample or a particular reference set of RNA transcripts (or their products). Normalization can be performed to correct for or normalize away both differences in the amount of biomarker assayed and variability in the quality of the biomarker type used. Therefore, an assay typically measures and incorporates the expression of certain normalizing polynucleotides or polypeptides, including well known housekeeping genes, such as, for example, GAPDH and/or actin. Alternatively, normalization can be based on the mean or median signal of all of the assayed biomarkers or a large subset thereof (global normalization approach).

To determine overexpression, the sample can be compared with a corresponding sample that originates from a healthy individual. That is, the "normal" level of expression is the level of expression of the biomarker in, for example, a breast tissue sample from an individual not afflicted with breast cancer. Such a sample can be present in standardized form. Sometimes, determining biomarker overexpression requires no comparison between the sample and a corresponding sample that originated from a healthy individual. For example, detecting overexpression of a biomarker indicative of a poor prognosis in a breast tumor sample may preclude the need for comparison to a corresponding breast tissue sample that originates from a healthy individual.

Methods of detecting and quantifying polynucleotide biomarkers in a sample are well known in the art. Such methods include, but are not limited to gene expression profiling, which are based on hybridization analysis of polynucleotides, and sequencing of polynucleotides. The most commonly used methods art for detecting and quantifying polynucleotide expression in include northern blotting and in situ hybridization (Parker & Barnes (1999) *Methods Mo/. Biol.* 106:247-283), RNAse protection assays (Hod (1992) *Biotechniques* 13:852-854), PCR-based methods, such as RT-PCR (Weis et al. (1992) TIG 8:263-264), and array-based methods (Schena et al. (1995) *Science* 270:467-470). Alternatively, antibodies may be employed that can recognize specific duplexes, including DNA duplexes, RNA duplexes, and DNA-RNA hybrid duplexes, or DNA-protein duplexes in, for example, an oligonucleotide-linked immunosorbent assay ("OLISA"). See, Lee et al. (1985) *FEBS Lett.* 190: 120-124; Han et al. (2010) *Bioconjug. Chem.* 21:2190-2196; Miura et al. (1987) *Biochem. Biophys. Res. Commun.* 144: 930-935; and Tanha & Lee (1997) *Nucleic Acids Res.* 25:1442-1449. Representative methods for sequencing-based gene expression analysis include Serial Analysis of Gene Expression ("SAGE") and gene expression analysis by massively parallel signature sequencing. See, Velculescu et al. (1995) *Science* 270: 484-487.

Isolated RNA can be used to determine the level of biomarker transcripts (i.e., mRNA) in a sample, as many expression detection methods use isolated RNA. The starting material typically is total RNA isolated from a body sample, such as a tumor or tumor cell line, and corresponding normal tissue or cell line, respectively. Thus, RNA can be isolated from a variety of primary tumors, including breast, lung, colon, prostate, brain, liver, kidney, pancreas, spleen, thymus, testis, ovary, uterus, and the like, or tumor cell lines. If the source of mRNA is a primary tumor, mRNA can be extracted, for example, from frozen or archived paraffin-embedded and fixed (e.g., formalin-fixed) tissue samples.

Methods of isolating polynucleotides such as RNA from a sample are well known in the art. See, e.g., *Molecular Cloning: A Laboratory Manual*, 3rd ed. (Sambrook et al. eds., Cold Spring Harbor Press 2001); and *Current Protocols in Molecular Biology* (Ausubel et al. eds., John Wiley & Sons 1995). Methods for RNA extraction from paraffin-embedded tissues also are well known in the art. See, e.g., Rupp & Locker (1987) *La.b Invest.* 56:A67; and De Andres et al. (1995) *Biotechniques* 18:42-44. Moreover, isolation/purification kits are commercially available for isolating polynucleotides such as RNA (Qiagen; Valencia, Calif.). For example, total RNA from cells in culture can be isolated using Qiagen RNeasy® Mini-Columns. Other commercially available RNA isolation/purification kits include Master-Pure™ Complete DNA and RNA Purification Kit (Epicentre; Madison, Wis.) and Paraffin Block RNA Isolation Kit (Ambion; Austin, Tex.). Total RNA from tissue samples can be isolated, for example, using RNA Stat-60 (Tel-Test; Friendswood, Tex.). RNA prepared from a tumor can be isolated, for example, by cesium chloride density gradient centrifugation. Additionally, large numbers of tissue samples readily can be processed using techniques well known to those of skill in the art, such as, for example, the single-step RNA isolation process of Chomczynski (U.S. Pat. No. 4,843,155).

Once isolated, the polynucleotide, such as mRNA, can be used in hybridization or amplification assays including, but not limited to, Southern or Northern blotting, PCR and probe arrays. One method of detecting polynucleotide levels involves contacting the isolated polynucleotides with a nucleic acid molecule (probe) that can hybridize to the desired polynucleotide target. The nucleic acid probe can be, for example, a full-length DNA, or a portion thereof, such as an oligonucleotide of at least about 10, 15, 20, 30, 40, 50, 75, 100, 125, 150, 175, 200, 225, 250, 275, 300, 400 or 500 nucleotides or more in length and sufficient to specifically hybridize under stringent conditions to a polynucleotide such as an mRNA or genomic DNA encoding a biomarker of interest. Hybridization of a polynucleotide encoding the biomarker of interest with the probe indicates that the biomarker in question is being expressed.

Stringent hybridization conditions typically include low ionic strength and high temperature for washing and can be defined as hybridizing at 68° C. in 5×SSC/5×Denhardt's solution/1.0% SOS, and washing in 0.2×SSC/0.1% SOS+/− 100 g/ml denatured salmon sperm DNA at room temperature (RT). Moderately stringent hybridization conditions include conditions less stringent than those described above (e.g., temperature, ionic strength and % SOS) and can be defined as washing in the same buffer at 42° C. One of skill in the art understands how to adjust the temperature, ionic strength, etc. as necessary to accommodate factors such as probe length and the like. Additional guidance regarding such conditions is readily available in the art, for example, in *Molecular Cloning: A Laboratory Manual*, 3rd ed. (Sambrook et al. eds., Cold Spring Harbor Press 2001); and Current Protocols in Molecular Biology (Ausubel et al. eds., John Wiley & Sons 1995).

Another method of detecting polynucleotide expression levels that involves immobilized polynucleotides on a solid surface such as a biochip or a microarray and contacting the immobilized polynucleotides with a probe, for example by running isolated mRNA on an agarose gel and transferring the mRNA from the gel to a membrane, such as nitrocellulose. Alternatively, the probes can be immobilized on a solid surface and isolated mRNA is contacted with the probes, for example, in an Agilent Gene Chip Array or Affymetrix GeneChip.

As used herein, "biochip" or "microarray" can be used interchangeably to mean a solid substrate comprising an attached probe or plurality of probes as described herein, wherein the probe(s) comprise at least about 1, 2, 3, 4, 5, 6, 7, 8, 9, 10, 11, 12, 13, 14, 15, 16, 17, 18, 19, 20, 25, 30, 35, 40, 45, 50, 100, 150, 200 or more probes. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The probes may be attached to the biochip/microarray in a wide variety of ways, as will be appreciated by one of skill in the art. The probes may either be synthesized first, with subsequent attachment to the biochip, or may be directly synthesized on the biochip/microarray. The solid substrate may be a material that may be modified to contain discrete individual sites appropriate for the attachment or association of the probes and is amenable to at least one detection method.

Examples of substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses and plastics. The substrates may allow optical detection without appreciably fluorescing. The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip/microarray and the probe can be derivatized with chemical functional groups for subsequent attachment of the two. For example, the biochip/microarray may be derivatized with a chemical functional group including, but not limited to, amino groups, carboxyl groups, oxo groups or thiol groups. Using these functional groups, the probes can be attached using functional groups on the probes either directly or indirectly using a linker. The probes may be attached to the solid support by either the 5' terminus, 3' terminus, or via an internal nucleotide. The probe may also be attached to the solid support noncovalently. For example, biotinylated oligonucleotides can be made, which may bind to surfaces covalently coated with streptavidin, resulting in attachment. Alternatively, probes can be synthesized on the surface using techniques such as photopolymerization and photolithography.

For example, microarrays can be used to detect polynucleotide expression. Microarrays are particularly well suited because of the reproducibility between different experiments. DNA microarrays provide one method for the simultaneous measurement of the expression levels of large numbers of polynucleotides. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138; 5,800,992; 6,020, 135; 6,033,860 and 6,344,316. High-density oligonucleotide arrays are particularly useful for determining expression profiles for a large number of polynucleotides in a sample. For example, the methods described herein used a microarray and 4 or 5 probes including 212022_s_at (MK167), 203145_at (SPAG5), 204817_at (ESPL1), 202240_at (PLK1).

Methods of synthesizing these arrays using mechanical synthesis methods are described in, for example, U.S. Pat. No. 5,384,261. Although a planar array surface generally is used, the array can be fabricated on a surface of virtually any shape or even a multiplicity of surfaces. Arrays can be nucleic acids (or peptides) on beads, gels, polymeric surfaces, fibers (such as fiber optics), glass or any other appropriate substrate. See, e.g., U.S. Pat. Nos. 5,770,358; 5,789,162; 5,708,153; 6,040,193 and 5,800,992.

As such, PCR-amplified inserts of cDNA clones can be applied to a substrate in a dense array. For example, at least about 10,000 nucleotide sequences can be applied to the substrate. The microarrayed genes, immobilized on the microchip at 10,000 elements each, are suitable for hybridization under stringent conditions. Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance.

With dual color fluorescence, separately labeled cDNA probes generated from two sources of polynucleotide can be hybridized pairwise to the array. The relative abundance of the transcripts from the two sources corresponding to each specified molecule is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. See, Schena et al. (1996) *Proc. Natl. Acad Sci. USA* 93:106-149. Advantageously, microarray analysis can be performed by commercially available equipment, following manufacturer's protocols, such as by using the Affymetrix® GenChip Technology, or Agilent® Ink-Jet Microarray Technology. The development of microarray methods for large-scale analysis of gene expression makes it possible to search systematically for molecular markers of cancer classification and outcome prediction in a variety of tumor types.

Another method of detecting polynucleotide expression levels involves a digital technology developed by NanoString® Technologies (Seattle, Wash.) and based on direct multiplexed measurement of gene expression, which offers high levels of precision and sensitivity (<1 copy per cell). The method uses molecular "barcodes" and single molecule imaging to detect and count hundreds of unique transcripts in a single reaction. Each color-coded barcode is attached to a single target-specific probe corresponding to a gene of interest. Mixed together with controls, they form a multiplexed CodeSet. Two ~50 base probes per mRNA can be included for hybridization. The reporter probe carries the signal, and the capture probe allows the complex to be immobilized for data collection. After hybridization, the excess probes are removed and the probe/target complexes aligned and immobilized in an nCounter® Cartridge. Sample cartridges are placed in a digital analyzer for data collection. Color codes on the surface of the cartridge are counted and tabulated for each target molecule.

Another method of detecting polynucleotide expression levels involves nucleic acid amplification, for example, by RT-PCR (U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad Sci. USA* 86:1173-1177), Q-Beta Replicase (Lizardi et al., (1988) *Bio/Technology* 6:1197), rolling circle replication (U.S. Pat. No. 5,854,033), or any other nucleic acid amplification method, followed by the detection of the amplified molecules using techniques well known in the art. Likewise, biomarker expression can be assessed by quantitative fluorogenic RT-PCR (i.e., the TaqMan® System). For PCR analysis, methods and software are available to determine primer sequences for use in the analysis. These methods are particularly useful for detecting polynucleotides present in very low numbers.

Additional methods of detecting polynucleotide expression levels of RNA may be monitored using a membrane blot (such as used in hybridization analysis such as Northern or Southern blotting, dot, and the like), or microwells, sample tubes, gels, beads or fibers (or any solid support comprising bound nucleic acids). See, e.g., U.S. Pat. Nos. 5,770,722; 5,874,219; 5,744,305; 5,677, 195 and 5,445,934. Polynucleotide biomarker expression also can include using nucleic acid probes in solution.

Another method of detecting polynucleotide expression levels involves SAGE, which is a method that allows the simultaneous and quantitative analysis of a large number of polynucleotides without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules that can be sequenced, revealing the identity of the multiple tags simultaneously. The expression pattern of any population of transcripts can be quantitatively evaluated by determining the abundance of individual tags and identifying the gene corresponding to each tag. See, Velculescu et al. (1995), supra.

Another method of detecting polynucleotide expression levels involves massively parallel signature sequencing ("MPSS"). See, Brenner et al. (2000) Nat. Biotech. 18:630-634. This sequencing combines non-gel-based signature sequencing with in vitro cloning of millions of templates on separate diameter microbeads. First, a microbead library of DNA templates can be constructed by in vitro cloning. This is followed by assembling a planar array of the template-containing microbeads i a flow cell at a high density (typically greater than $3.0 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast DNA library.

After measuring expression levels of the biomarkers, the methods then include correlating the expression levels of the biomarkers in the patient sample to a reference/control set to determine the prognosis of the patient. One can use any method available for correlating expression levels of polynucleotide (or polypeptide) biomarkers.

The Examples below describe a modified AP relapse test in which the binary classification value is replaced with a continuous risk score that measures probability that the patient is considered high risk for relapse.

The AP test can employ a computer to perform the test. For example, a computer running a software program can analyze biomarker expression level data from a patient, compare that data to a distribution of expression levels from a population of patients having the same disease state, and determine whether the patient's expression levels have a +/−AP status for each biomarker of interest. Based on the AP status for each biomarker, the computer software can determine the prognosis for the patient as being good or poor. For example, the software can generate a report summarizing the patient's biomarker expression levels and/or the patient's AP status scores, and/or a prediction of the likelihood of long term survival of the patient and/or the likelihood of recurrence or metastasis of the patient's disease condition, for example, cancer. Moreover, the computer program can perform any statistical analysis of the patient's data or a population of patient's data as described herein in order to generate the AP status of the patient. Further, the computer program also can normalize the patient's biomarker expression levels in view of a standard or control prior to comparison of the patient's biomarker expression levels to those of the patient population. The computer also can ascertain raw data of a patient's expression values from, for example, immune-histochemical staining or a microarray, or the raw data can be input into the computer.

Methods for assessing statistical significance are well known in the art and include, for example, using a log-rank test, Cox analysis and Kaplan-Meier curves. A p-value of less than 0.05 can be used to constitute statistical significance.

Overexpression of a biomarker or combination of biomarkers of interest in a sample can be indicative of a poor cancer prognosis. As used herein, "indicative of a poor prognosis" is intended that altered expression of particular biomarkers or combination of biomarkers is associated with an increased likelihood of relapse or recurrence of the underlying cancer or tumor, metastasis or death. For example, "indicative of a poor prognosis" may refer to an increased likelihood of relapse or recurrence of the underlying cancer or tumor, metastasis, or death within 10 years, such as 5 years or even 3 years. The absence of overexpression of a biomarker or combination of biomarkers of interest is indicative of a good prognosis. As used herein, "indicative of a good prognosis" refers to an increased likelihood that the patient will remain cancer free. For example, "indicative of a good prognosis" may refer to an increased likelihood that the patient will remain cancer-free for 10 years, such as 5 years or even 3 years.

Likewise, and as noted above, it is contemplated that the methods herein can be applied to polypeptide biomarkers, as methods of detecting and quantifying polypeptides in a sample are well known in the art and include, but are not limited to, immunohistochemistry and proteomics-based methods.

EXAMPLES

The invention will be more fully understood upon consideration of the following non-limiting examples, which are offered for purposes of illustration, not limitation.

Example 1:—Materials and Methods, Five Gene Panel Screening Assay/MicroArray Datasets The Microarray Datasets Used in this Study RNA from primary tumor samples was hybridized to the hgu133a v2 array platform to form Affymatrix dataset for this study (Table 2). The training set consists of the LN- samples in the GSE3494 and the GSE7390 (Gene Expression Omnibus, www.ncbi.nlm.nih.gov).

This study used all ER+, lymph node negative samples in the cohorts listed in Table 2.

The Metabric dataset (Table 2 (infra), Curtis et al. [16]) contains gene expression values hybridized to the illumina-Humanv3 array platform. Patients that were treated with systemic chemotherapy were removed for this study. Death due to breast cancer is the survival endpoint in this dataset.

The prognostic significance of INDUCT will be studied with respect to the two endpoints: metastasis-free survival (Affymetrix; Table 2) and breast cancer specific survival (Metabric). The terms relapse-free survival, expected survival and event-free survival may be used to refer to one or the other of these possible endpoints.

Translation of the Microarray Gene Set to qRT-PCR Platform Using Formalin-Fixed. Paraffin-Embedded Tissues Sample Selection and Preparation Archival formalin-fixed, paraffin-embedded (FFPE) tumor blocks were chosen from patients with breast cancer at the Indiana University Simon Cancer Center based on their Oncotype DX RS. Initial real-time quantitative RT-PCR (qRT-PCR) analysis was conducted using 10 samples of ER+ breast cancers. This was followed by qRT-PCR analysis using customized arrays of 23 cases with high RS, 26 cases with intermediate RS, and 23 cases with low RS. Demographic and clinical characteristics of the patients were acquired from medical charts (Table S1). The cases were equally divided into training and validation sets, each of 36 cases. The distribution of RS in the training set was shown to be significantly equivalent to the distribution of RS in validation set using the Kolmogorov-Smirnoff test (P value=0.88).

TABLE S1

The clinical characteristics of patients with Oncotype Dx scores are shown. All patients were ER-positive and HER-negative by clinical assays and did not involve nodal metastasis.

| Patient # | Age | Tumor size (cm) | Grade | RS score | low/intermed/high |
|---|---|---|---|---|---|
| Patient 1 | 48 | 0.8 | 1 | 18 | IS |
| Patient 2 | 46 | 2.7 | 1 | 7 | LS |
| Patient 3 | 49 | 1.5 | 2 | 8 | LS |
| Patient 4 | 34 | 2.3 | 2 | 23 | IS |
| Patient 5 | 63 | 1.9 | 2 | 30 | IS |
| Patient 6 | 40 | 2.5 | 3 | 28 | IS |
| Patient 7 | 45 | 1.5 | 2 | 7 | LS |
| Patient 8 | 48 | 0.7 | 1 | 27 | IS |
| Patient 9 | 58 | 2.5 | 2 | 0 | LS |
| Patient 10 | 49 | 2.7 | 2 | 25 | IS |
| Patient 11 | 48 | 1.5 | 1 | 13 | LS |

TABLE 2

Patient characteristics in the microarray datasets

| GEO Series | GSE3494 | GSE7390 | GSE12093 | GSE6532 | GSE2034 | GSE11121 | GSE17705 |
|---|---|---|---|---|---|---|---|
| Cohort code | UPPS | TRANSBIG | VER2 | OXFD | VDX | MZ | MDA |
| # Estrogen receptor+ | 202 | 135 | 136 | 144 | 205 | 169 | 289 |
| Lymph node (−/+/NA) | 131/65/6 | 135/0/0 | 136/0/0 | 102/36/6 | 205/0/0 | 169/0/0 | 170/108/0 |
| Tamoxifen (yes/no/NA) | 61/141/0 | 0/135/0 | 136/0/0 | 99/45/0 | 0/205/0 | 0/169/0 | 289/0/0 |
| Grade (1/2/3/NA) | 63/112/25/2 | 28/72/34/1 | NA | 29/59/23/34 | NA | 29/123/17/0 | NA |
| Size (≥2 cm/<2 cm/NA) | 97/105/0 | 54/98/0 | NA | 54/88/0 | NA | 88/81/0 | NA |
| Age (≥50/<50/NA) | 35/167/0 | 88/47/0 | NA | 22/120/0 | NA | NA | NA |

TABLE S1-continued

The clinical characteristics of patients with Oncotype Dx scores are shown. All patients were ER-positive and HER-negative by clinical assays and did not involve nodal metastasis.

| Patient # | Age | Tumor size (cm) | Grade | RS score | low/intermed/high |
|---|---|---|---|---|---|
| Patient 12 | 44 | 1.3 | 3 | 17 | LS |
| Patient 13 | 50 | 1.2 | 1 | 6 | LS |
| Patient 14 | 66 | 1.5 | 2 | 21 | IS |
| Patient 15 | 67 | 1.1 | 1 | 3 | LS |
| Patient 16 | 55 | 1.5 | 2 | 21 | IS |
| Patient 17 | 40 | 0.7 | 1 | 21 | IS |
| Patient 18 | 75 | 0.7 | 2 | 12 | LS |
| Patient 19 | 53 | 3.5 | 1 | 16 | LS |
| Patient 20 | 67 | 1.3 | 2 | 32 | HS |
| Patient 21 | 47 | 1.1 | 2 | 13 | LS |
| Patient 22 | 38 | 2 | 2 | 39 | HS |
| Patient 23 | 47 | 1.1 | 2 | 19 | IS |
| Patient 24 | 59 | 3.5 | 2 | 4 | LS |
| Patient 25 | 62 | 1.4 | 2 | 19 | IS |
| Patient 26 | 56 | 1.6 | 2 | 22 | IS |
| Patient 27 | 41 | 3 | 2 | 24 | IS |
| Patient 28 | 55 | 1.8 | 3 | 32 | HS |
| Patient 29 | 58 | 1.6 | 3 | 46 | HS |
| Patient 30 | 73 | 1.3 | 2 | 33 | HS |
| Patient 31 | 49 | 0.4 | 2 | 32 | HS |
| Patient 32 | 69 | 3.8 | 2 | 39 | HS |
| Patient 33 | 55 | 2.8 | 3 | 44 | HS |
| Patient 34 | 54 | 1.8 | 3 | 27 | IS |
| Patient 35 | 53 | 2 | 2 | 22 | IS |
| Patient 36 | 29 | 0.9 | 2 | 22 | IS |
| Patient 37 | 56 | 2 | 2 | 22 | IS |
| Patient 38 | 57 | 1.8 | 3 | 34 | HS |
| Patient 39 | 58 | 1.1 | 2 | 31 | HS |
| Patient 40 | 44 | 1.5 | 2 | 42 | HS |
| Patient 41 | 36 | 1.6 | 3 | 65 | HS |
| Patient 42 | 69 | 0.9 | 1 | 16 | LS |
| Patient 43 | 67 | 1.3 | 3 | 21 | IS |
| Patient 44 | 38 | 1.9 | 2 | 21 | IS |
| Patient 45 | 56 | 1.8 | 2 | 21 | IS |
| Patient 46 | 76 | 3.5 | 2 | 33 | HS |
| Patient 47 | 51 | 3 | 2 | 36 | HS |
| Patient 48 | 44 | 2.3 | 3 | 37 | HS |
| Patient 49 | 72 | 0.2 | 2 | 7 | LS |
| Patient 50 | 52 | 3.1 | 2 | 18 | LS |
| Patient 51 | 27 | 1.5 | 2 | 16 | LS |
| Patient 52 | 67 | 1.7 | 2 | 38 | HS |
| Patient 53 | 62 | 2 | 3 | 34 | HS |
| Patient 54 | 35 | 2 | 3 | 31 | HS |
| Patient 55 | 30 | 2.5 | 3 | 22 | IS |
| Patient 56 | 66 | 1 | 2 | 26 | IS |
| Patient 57 | 49 | 0.6 | 1 | 18 | LS |
| Patient 58 | 54 | 1.8 | 2 | 6 | LS |
| Patient 59 | 45 | 1.3 | 2 | 18 | LS |
| Patient 60 | 69 | 2.3 | 2 | 20 | IS |
| Patient 61 | 49 | 1.1 | 2 | 20 | IS |
| Patient 62 | 50 | 3 | 3 | 42 | HS |
| Patient 63 | 34 | 1.3 | 3 | 43 | HS |
| Patient 64 | 76 | 2.8 | 2 | 34 | HS |
| Patient 65 | 43 | 1.7 | 2 | 25 | IS |
| Patient 66 | 62 | 1.1 | 2 | 27 | IS |
| Patient 67 | 50 | 0.6 | 2 | 21 | IS |
| Patient 68 | 70 | 1 | 2 | 49 | HS |
| Patient 69 | 64 | 2.2 | 2 | 50 | HS |
| Patient 70 | 62 | 1.5 | 2 | 12 | LS |
| Patient 71 | 45 | 1.3 | 3 | 18 | LS |
| Patient 72 | 68 | 2 | 1 | 9 | LS |

RNA was extracted from 10 μm-thick sections of archival paraffin blocks using RecoverAll™ Total Nucleic Acid Isolation Kit (Life Technologies, Grand Island, N.Y.) according to the manufacturer's instructions. The quality of RNA was assessed using the Nanodrop® ND-1000 spectrophotometer (ThermoScientific, Wilmington, Del.). Total RNAs were reverse-transcribed using the High Capacity cDNA Reverse Transcription kit (Life Technologies) according the manufacturer's instructions.

Selection of the TaqMan qRT-PCR Assays

Specific target sequences for each probe from Human Genome U133A 2.0 Array were obtained using NetAffx Analysis Center <http://www.affymetrix.com/analysis/index.affx>. Target sequences were aligned to the appropriate mRNA reference sequence (REFSEQ) accession number using NCBI BLAST (Basic Local Alignment Search Tool) <http://blast.ncbi.nlm.nih.gov/Blast.cgi> and accessed the consensus sequence through the NCBI Entrez nucleotide database.

Using UMapIt mapping tool of Applied Biosystems (ABI, Foster City, Calif.), the Affymetrix probe IDs were mapped to TaqMan assays specific to each sequence. TaqMan assays, where necessary custom-designed using Primer Express (Applied Biosystems), were tested for the amplification efficiency based on the ABI defined criteria. Control RNA (Universal Human Reference RNA; Stratagene) and FFPE samples were used to test the efficiency of the probes. Based on the observed efficiency, probes were selected for custom array microfluidic cards (TaqMan assays; Table S2).

TABLE S2

TaqMan Custom Array Format 16_INDUCT

| # genes | Gene Symbol | Assay ID | Amplicon length |
|---|---|---|---|
| 1 | MKI67 | Hs04260396_g1 | 64 |
| 2 | SPAG5 | Hs04260397_s1 | 60 |
| 3 | ESPL1 | Hs00901789_g1 | 62 |
| 4 | CDC6 | Hs00154374_m1 | 77 |
| 5 | CDC46L | Hs00907337_m1 | 62 |
| 6 | CDT1 | Hs00368864_m1 | 59 |
| 7 | PLK1 | Hs00983233_g1 | 61 |
| 8 | PHLPP1 | Hs01597874_m1 | 90 |
| 9 | CENPA | Hs00903938_g1 | 62 |
| 10 | CXCL9 | Hs00171065_m1 | 60 |
| 11 | PRPF4 | Hs00992013_g1 | 73 |
| 12 | ACTB *** | Hs00357333_g1 | 77 |
| 13 | TFRC *** | Hs00951083_m1 | 66 |
| 14 | GUS *** | Hs99999908_m1 | 81 |
| 15 | RPLPO *** | Hs99999902_m1 | 105 |
| 16 | GAPDH *** | control in the array | | qRT-PCR Analysis Using Custom Arrays

TaqMan reactions were performed in triplicates using custom array microfluidic cards preloaded with TaqMan Gene Expression Assays containing 16 genes (11 discriminant genes and five reference genes) on an ABI Prism 7900HT Fast Real-Time platform according to the manufacturer's instructions (Table S2). ACTB, TFRC, GUS, RPLPO, and GAPDH were used as endogenous reference controls for normalization. Delta threshold cycle values for each of the 11 genes of interest were normalized using these endogenous controls according to the method of Applied Biosystems DataAssist™ Software v3.0.

Statistical Analyses

All statistical analysis were performed using R, www.r-project.org). Mixture models were fit using the package mclust [17, 1], and survival analysis was performed with the survival package. The significance of a Cox proportional hazard (CPH) model is assessed with the P value of the log rank score test. The significance of a multivariant CPH over a CPH using a subset of the variables is measured with a Chi-squared test of the log-likelihoods. The proportional hazard condition is tested with the cox.zph function. The Cox spline [19] method of fitting a survival model to a continuous variable was implemented with the rms R package.

Construction of a Relapse Risk Score from Gene Expression Measurements

A gene is considered multistate [12] if its distribution of expression across a population is sufficiently bimodal, which is formalized with the statistical concept of a mixture model. In building prognostic models, the continuous vector of expression values for a multistate gene is replaced by a binary variable representing the two components. By convention, the component enriched with poor prognosis cases is given the value 1 and the other component the value 0. The prognostic model defined in [12] uses four multistate genes and labels a patient as poor prognosis if the sum of the four corresponding binary variables is greater than 0. The features that define a multistate model in a sample set are the choice of genes and the thresholds separating the high and low components. One weakness of this approach is that samples near the threshold may be misclassified.

In this study, uncertainty about the value of the threshold is built into the model by replacing the binary classification variable by a continuous score that measures probability of membership in a component; i.e., numbers near 0, 1, or in between depending on the likelihood that the sample is in the poor prognosis component. This risk score for a gene is produced by the mixture model methods. The risk score for a gene derived from the mixture model fit in a training set is generalized to a validation set using the statistical method of fitting the same mixture model to the new data.

A prognostic score for a panel of multistate genes is defined as the sum of the risk scores of these genes. This contrasts with the method described by Buechler [12] in which the multigene prognostic variable is 1 if any of single-gene variables is 1, and 0 otherwise. Here, samples considered low risk by all of the genes will have a score near 0, and the score increases with the number of genes that classify the sample as high risk.

Workflow of this Study

Figure 7:
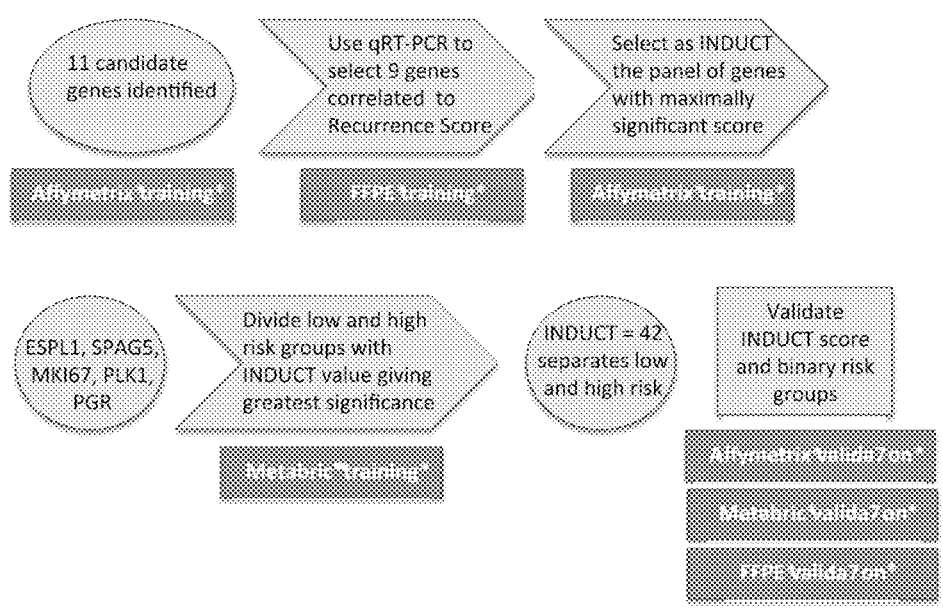
FIG. 7. The steps used in the derivation and validation of the INDUCT prognostic test are charted here. Sets of samples used in particular steps are indicted below the steps. The continuous INDUCT score is derived in steps A-C using both the Affymetrix and FFPE training sets. The binary INDUCT test, which separates patients into low risk and high risk groups (step D) is derived in the Metabric training set. The significance of the resulting continuous and binary INDUCT tests are then assessed in the Affymetrix, Metabric and FFPE validation sets.

Starting with preliminary results from the AP4 study [12], the continuous INDUCT score is derived in the Affymetrix training set (FIG. 7, steps A, C), with a requirement that the panel genes are significant in the FFPE training set (FIG. 7, step B). A binary risk stratification in which INDUCT<42 defines the low risk group and INDUCT 42 defines the high risk group is derived by selecting the INDUCT threshold giving the most significant binary variable (in a CPH) in the Metabric training set (FIG. 7, step D). The resulting tests are then validation in multiple cohorts using three different technologies for measuring gene expression. The significance of INDUCT in comparison to clinico-pathological variables and Tamoxifen treatment status is then assessed.

Example 2:—INDUCT: A Continuous Score Using Expression Values of ESPL1, MK167, SPAG5, PLK1 and PGR A set of 11 genes plus the addition of a PGR gene, is examined in the present example (FIG. 7, step A). This set of 12 genes were ESPL1, CDC45L, PLK1, CENPA, MKI67, SPAG5, CDT1, PRG, CXCL9, CDC6, PHLPP1, and PRPF4.

To validate, a qRT-PCR analysis of these 12 genes were first examined in a training set of 36 ER+ breast cancer FFPE samples with known Oncotype DX RS (Table 3).

TABLE 3

Characteristics of the patients in the FFPE datasets used in this study

|  | FFPE training set | FFPE validation set |
|---|---|---|
| Number | 36 | 36 |
| Age (<50/≥50) | 15/21 | 15/21 |
| Grade (1/2/3) | 8/21/7 | 3/24/9 |
| Size (≤2 cm />2 cm) | 24/12 | 29/7 |
| TAILORx risk groups (LR/IR/HR) | 4/18/14 | 6/15/15 |
| Oncotype Dx risk groups (LR/IR/HR) | 9/16/11 | 9/15/12 |

Figure 8:
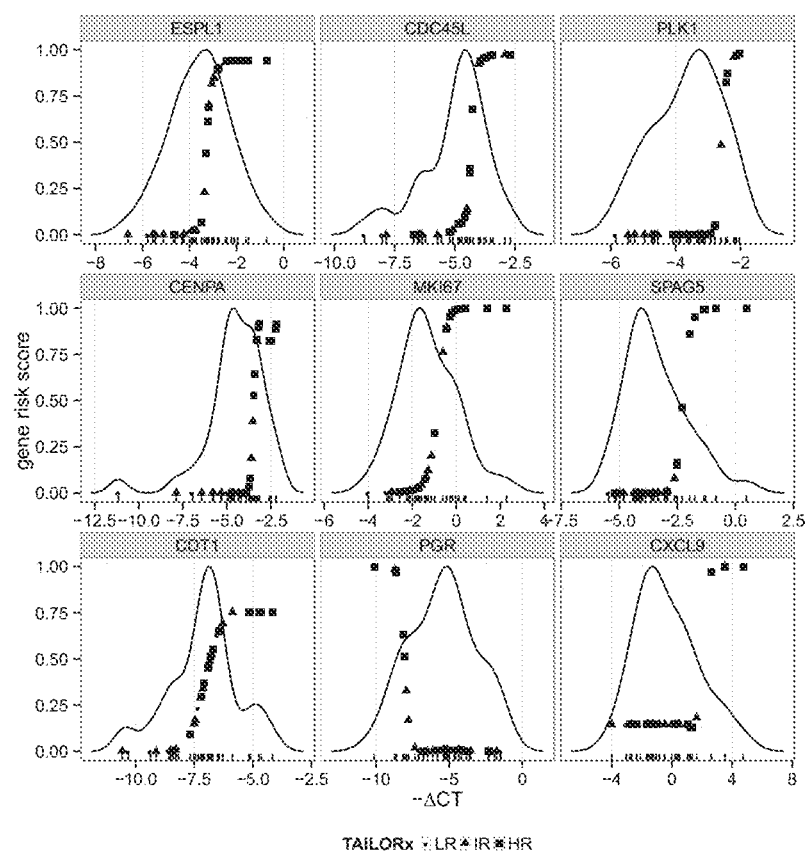
FIG. 8. The risk score calculated from components of the mixture model fit versus the expression values are plotted for the 12 candidate genes. The density distributions of expression values, scaled to 0-1, are superimposed on the plot. The points are marked by the TAILORx risk category, showing that for each of these genes nearly all of the points in the high component are in the high risk category. In an ANOVA test of the risk score against the TAILORx risk groups the P values are ESPL1 (0.00026), CDC45L (0.00051), PLK1 (0.00055), CENPA (0.0017), MK167 (0.0025), SPAG5 (0.026), CDT1 (0.033), PGR (0.045), CXCL9 (0.046), PHLPP1 (0.253), CDC6 (0.297), and PRPF4 (0.39).

For each of the 12 target genes on the qRT-PCR Array, a mixture model was fit to the distribution of Δ-CT values on the training set of 36 samples (FIG. 7, step B). Risk scores derived from the mixture models (Methods) were plotted against Δ-CT values (FIG. 8) and colored by TAILORx risk groups, illustrating the connection between the risk scores and RS. Formally, a gene's correlation with RS is assessed by an ANOVA test of the risk score against the TAILORx risk groups (data reported in the legend of FIG. 8). The genes are ordered in FIG. 8 by level of significance, and the nine genes (ESPL1, CDC45L, PLK1, CENPA, MK167, SPAG5, CDT1, PRG, CXCL9), with associated P value of <0.05 were considered for inclusion in INDUCT. The partition of each of the genes into components is based solely on the distribution of the expression values. The TAILORx risk groups are only used to guide the selection of genes to include in the model.

The nine genes identified by the above method (ESPL1, CDC45L, PLK1, CENPA, MKI67, SPAG5, CDT1, PGR, CXCL9), were then used to develop an Affymetrix-probe based prognostic score using the 266 ER+/lymph node negative (LN−) samples in the training set (FIG. 7, step C). The gene with the most significant risk score in a CPH model, namely, ESPL1, was selected materially for the panel. The second gene (MKI67) is the one with a very significant score, based on results from adding the gene's risk score to ESPL1. Continuing this process until the multigene score reaches a significant result in the panel, ESPL1, MKI67, SPAG5 and PLK1.

In some embodiments using specific gene processes, the risk score defined from these four genes ESPL1, MKI67, SPAG5 and PLK1, was not significantly improved by including additional genes. In other embodiments, the inclusion of PGR in the final panel results in a score that defines a larger set of good prognosis samples (8-year relapse-free survival>0.90) than any scores defined with fewer genes. Thus, in another embodiment of the panel, the 5 genes examined are ESPL1, MKI67, SPAG5, PLK1 and PGR:

As provided in some embodiments, the present screening panel comprises a novel combination of molecular probes: 204817_at (ESPL1), 212022_s_at (MKI67), 203145_at (SPAG5), 202240_at (PLK1), 208305_at (PGR). INDUCT score is the risk score defined by adding the individual gene risk scores of these five genes and scaling to the interval 0-100. This specific and unique combination of molecular probes provide a focused and efficient tool for identifying patients in the present INDUCT prognostic/diagnostic screening tool.

Example 3:—INDUCT is Translated to the Illumina Array Platform and a Threshold Between Low and High Risk Groups is Selected The INDUCT score was translated to the llumina illuminaHumanv3 array platform using the Metabric training data (Table 3).

TABLE 3

Characteristics of the patients in the microarray datasets used in this study

|  | Affymetrix | | Metabric | |
| --- | --- | --- | --- | --- |
|  | training* | validation† | training | validation |
| number | 266 | 1003 | 207 | 1147 |
| lymph node (−/+) | 266/0 | 782/221 | 200/7 | 603/544 |
| Tamoxifen (yes/no) | 15/251 | 568/435 | 0/207 | 954/193 |
| grade (1/2/3/NA) | 80/141/43/2 | 36/100/37/830 | 28/133/46/0 | 129/523/427/68 |
| size (≤2 cm/>2 cm/NA) | 162/102/0 | 91/116/796 | 138/69/0 | 492/642/13 |
| Age (<50/≥50/NA) | 110/156/0 | 34/173/796 | 60/147/0 | 121/1026/0 |
| LN−, Tamoxifen-treated (events) | 15 (3) | 369 (45) | 0 | 422 (38) |

*GSE3494, GSE7390
†GSE12093, GSE6532 (Oxford cohort), GSE2034, GSE11121, GSE17705

Probes representing the 5 INDUCT genes were selected. If there were multiple probes for a given gene, the probe with maximum variance in the training set was chosen. For each panel gene, Mclust was applied to the vector of expression values in the Metabric training set to produce a mixture model fit and a risk score produced as described above for the Affymetrix training set: the INDUCT score is the sum of these scaled to 0-100.

A binary partition of patients into low risk and high risk groups was derived from the INDUCT score using the Metabric training set (FIG. 7, step D). For possible thresholds, $25 \leq c \leq 80$, form a binary variable that separates tumors with INDUCT<c from those with INDUCT≥c, and compute a Cox proportional hazard model using this variable. As the threshold, one between INDUCT low risk and INDUCT high risk was selected as the value that defines the most significant survival model, namely c=42.

Figure 9A:
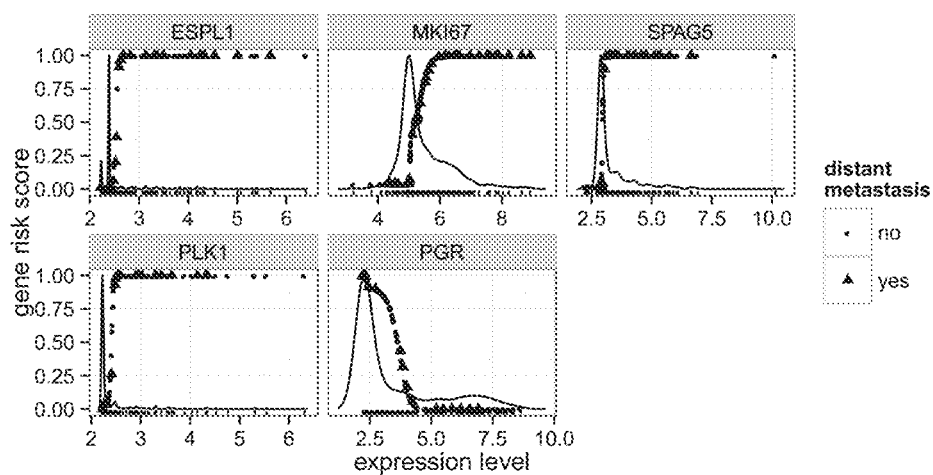
FIG. 9A-FIG. 9B. The risk score is plotted versus the expression values for the 5 INDUCT panel genes in FIG. 9A the Affymetrix validation set and FIG. 9B the Metabric validation set. The density distributions for the genes, scaled to 0-1, are superimposed on plots. Relapse event status is indicated by the shape of the points.
Figure 9B:
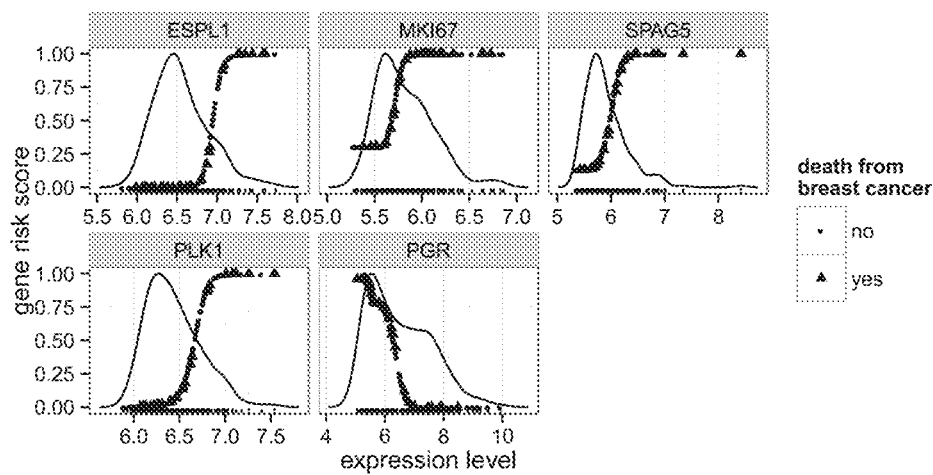

Example 4:—INDUCT Score Predicts Outcomes in Databases Produced with Affymetrix and Illumina Microarrays INDUCT was defined in the Affymetrix and Metabric validation sets by extending the mixture model fits from the corresponding training data to the new sets of expression values (Methods). FIG. 9 illustrates the relationship between the expression values of the genes and the risk scores in the two validation sets. The risk score of each panel gene is a significant risk factor in both of the validation sets.

The principal clinical application of INDUCT will be to select those ER+, LN− patients who can be safely treated with endocrine therapy alone instead of endocrine therapy and systemic chemotherapy. For this reason, our validation tests will focus on the LN− Tamoxifen treated samples.

The continuous INDUCT score is significantly prognostic in the LN− Tamoxifen treated samples (Table 3) in the Affymetrix validation set ($p=1.4 \times 10-9$) and the Metabric validation set (p=0.003). The expected event-free survival curves (FIG. 10) of LN− Tamoxifen-treated samples in the validation sets are above 0.90 for INDUCT scores<42 (the vertical line in the figure), after which the survival probability decreases rapidly.

Example 5:—INDUCT in FFPE Tissue is Concordant with the Oncotype DX Recurrence Score For the genes in the panel, the individual risk scores were extended from the FFPE training set to the validation set of FFPE samples (Methods) and the continuous INDUCT score computed as above. In particular, a Taqman Low Density Array was created for the genes MKI67, ESPL1, SPAG5, and PLK1 (Table S2); augmented with an RT-PCR probe for PGR, to measure mRNA levels from FFPE tumor samples. The Oncotype DX RS is linearly dependent (FIG. 11) on INDUCT ($P=6.4 \times 10-4$, R2=0.27). The binary risk stratification of the validation set of FFPE tissue defined with an INDUCT threshold of 42 significantly overlaps with categorical variables defined with the Oncotype DX RS cutoffs (P=0.03) and the TAILORx cutoffs (P=0.004).

Example 6:—INDUCT Defines a Low Risk Group Consisting of at Least 68% of LN− Tamoxifen-Treated Samples with 8-Year Relapse-Free Survival >0.92

Figure 12A:
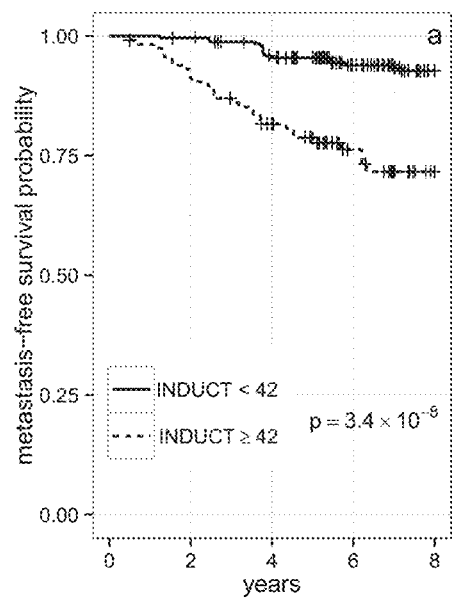
FIG. 12A-FIG. 12B. Kaplan-Meier survival plots for the discrete version of INDUCT in the LN−, Tamoxifen-treated samples in FIG. 12A the Affymetrix validation set and FIG. 12B the Metabric validation set. Table 5 contains detailed information about the sizes of the risk groups and the expected relapse-free survival probabilities in these groups.
Figure 12B:
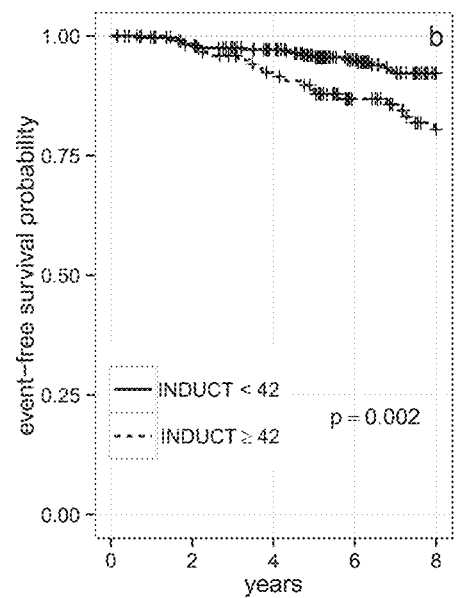

The present example demonstrates that the partitions into low and high risk groups defined by INDUCT=42 in the Affymetrix and Metabric LN− Tamoxifen-treated validation sets are significantly prognostic (FIG. 12 and Table 5).

TABLE 5

Characteristics of the low and high risk groups defined by INDUCT in the LN-Tamoxifen-treated microarray validation sets

|  | Affymetrix validation set | | Metabric validation set | |
| --- | --- | --- | --- | --- |
|  | Samples (events) | Expected survival (95% CI) | Samples (events) | Expected survival (95% CI) |
| TOTAL | 369 (45) | 0.86 (0.83-0.90) | 422 (38) | 0.89 (0.85-0.92) |
| Low INDUCT | 251 (16) | 0.93 (0.89-0.96) | 298 (18) | 0.92 (0.89-0.96) |
| High INDUCT | 116 (29) | 0.72 (0.63-0.81) | 123 (20) | 0.81 (0.73-0.89) |

Most notably, while the Oncotype DX Low Risk group is about 50% of LN− Tamoxifen-treated samples, the low risk groups defined by INDUCT are significantly larger and have comparable expected survival (68% of samples with 8-year metastasis-free survival 0.93 (95% CI 0.89-0.96) in Affymetrix; 71% of samples with 8-year event-free survival 0.92 (95% CI 0.89-0.96) in Metabric).

Example 7:—INDUCT is Significantly Prognostic Independent of Lymph Node Status and Tamoxifen Treatment Status INDUCT was defined in the ER+, LN− samples of the Affymetrix training set, however it is also significant in LN+ samples and is independent of Tamoxifen treatment status (Table 6).

TABLE 6

Significance of INDUCT in LN+/− and Tamoxifen treated and untreated subgroups†

|  | Affymetrix validation set | | | Metabric validation set | | |
| --- | --- | --- | --- | --- | --- | --- |
|  | number | events | INDUCT p-value | number | events | INDUCT p-value |
| LN− | 782 | 156 | <2 × 10−16 | 603 | 53 | 9.9 × 10−5 |
| LN+ | 221 | 70 | 0.03 | 544 | 122 | 8.6 × 10−10 |
| TAM+ | 586 | 108 | 3.7 × 10−7 | 954 | 159 | 2.6 × 10−10 |
| TAM− | 435 | 118 | 1.4 × 10−13 | 193 | 16 | 0.001 |

TABLE 6-continued

Significance of INDUCT in LN+/− and Tamoxifen treated and untreated subgroups†

| | Affymetrix validation set | | | Metabric validation set | | |
|---|---|---|---|---|---|---|
| | number | events | INDUCT p-value | number | events | INDUCT p-value |
| LN−, TAM+ | 369 | 45 | $1.4 \times 10^{-9}$ | 442 | 38 | 0.003 |
| LN−, TAM− | 413 | 111 | $3.9 \times 10^{-13}$ | 181 | 15 | 0.01 |

†TAM+ = Tamoxifen treated, TAM− = Tamoxifen untreated. Almost all LN+ samples were treated with Tamoxifen, so we do not further subdivide that group.

In multivariate analysis, the continuous INDUCT score and lymph node status are independent risk factors in the ER+ Metabric validation set. The most significant multivariate model in ER+ breast cancer using INDUCT and pathological and clinical variables includes INDUCT, lymph node status and tumor size (score test=137 on 3 degrees of freedom, $P<10-16$).

Tamoxifen treatment significantly lowers the risk of relapse in both the INDUCT low risk (P=0.0084, HR=0.49 (95% CI 0.29-0.84) and INDUCT high risk (P=0.0007, HR=0.50 (95% CI 0.36-0.75) subgroups of ER+, LN− breast cancer (Affymetrix dataset). This result contrasts with the apparent ineffectiveness of Tamoxifen treatment in the Oncotype DX high risk group[20].

Example 8:—INDUCT is Significant Independent of Clinico-Pathological Variables in LN− Tamoxifen-Treated Samples Clinico-pathological variables were shown to not improve the prognostic significance of INDUCT by adding the variables to INDUCT in a multivariate CPH model in the LN−Tamoxifen treated Metabric validation set. The variables, together with the P values for their coefficients when included with the INDUCT score in a CPH are: tumor size (0.11), patient age (0.29), grade (0.28) and ERBB2 status (0.85).

Figure 13:
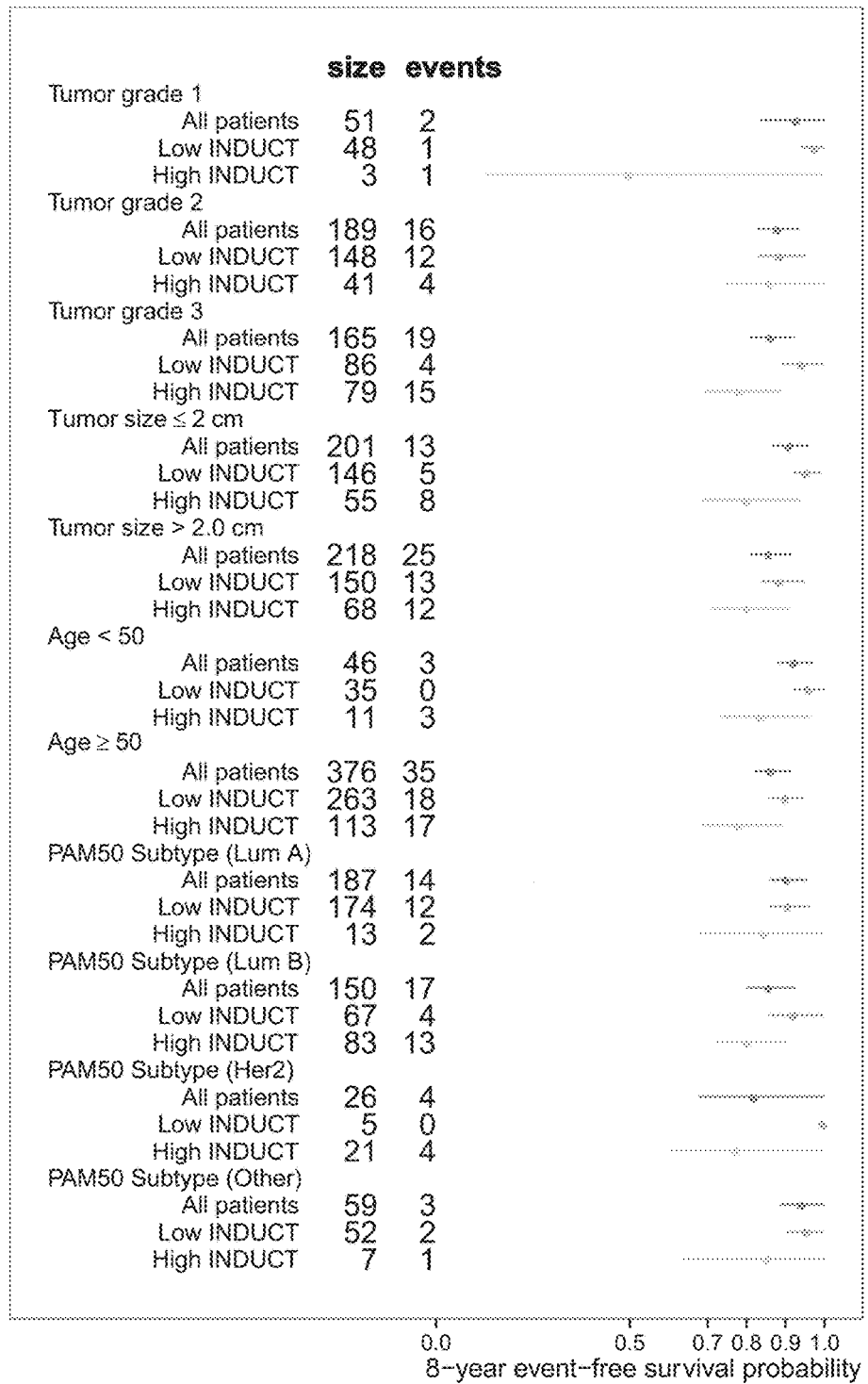
FIG. 13. 8-year expected survival probabilities for the INDUCT risk strata in clinically defined subgroups of the LN− Tamoxifen-treated samples in the Metabric validation set. The population-wide expected survival probability in this set is 0.89. The bar indicates the 95% confidence interval around the predicted probability (the point).

The INDUCT low risk group (INDUCT<42) and high risk group (INDUCT≥42) consistently have 8-year expected survival probabilities above and below 0.90, respectively, in subgroups defined by clinico-pathological variables and PAM50 subtypes (FIG. 13).

Example 9:—EarlyR Prognostic Score has Comparable Prognostic Strength to INDUCT

The INDUCT assessment tool provided in the present disclosure has superior performance characteristics compared to existing commercially available prognostic and diagnostic tools for breast cancer. However, the size of the intermediate risk group is difficult to assess. The following alternative formulation of a prognostic score from the same gene panel rectifies this problem.

To motivate the definition of EarlyR consider the mixture model fits of the expression values of the panel genes in the training set. Each gene's mixture model fit produces a subset of the training set that is termed here the high-risk component. The high risk component is defined by a threshold of the gene's expression values. The gene risk score is the probability that a sample is in the high-risk component, as assessed by the mixture model fit. The INDUCT score is the sum of the gene risk scores, scaled from 0 to 100. The fact that the gene risk score is near 1 or near 0 for almost all samples means that sums of the scores increase significantly only when multiple gene risk scores are near 1.

High score values are only attained when multiple genes are in a high-risk state. In the particular case of INDUCT, a score of 42 is only reached when at least 2 genes are in a high-risk state. From an analysis of the score values in the training set, the present investigators found that the set of samples with INDUCT≥42 is equivalent to the set S of samples for which any pair of panel genes are in a high risk state besides the pair MKI67 and PGR. More explicitly, S consists of the union of the intersections of the high-risk components for all pairs except MKI67 and PGR.

The EarlyR score is defined as the probability that a sample is in the set S described above. Considering the risk score for an individual panel gene as the probability function for membership in the gene's high-risk component, EarlyR can be calculated using formulas from probability theory as follows.

Calculation of EarlyR.

For a population of samples P, let rs(ESPL1), rs(SPAG5), rs(MKI67), rs(PLK1), rs(PGR) denote the risk scores of the panel genes in P. Let X be the set of pairs, (x,y), for x and y distinct panel genes except MKI67 and PGR. Then, $EarlyR = 1 - \Pi\{(x,y) \text{ in } X\}(1 - rs(x) \cdot rs(y))$.

Figure 14:
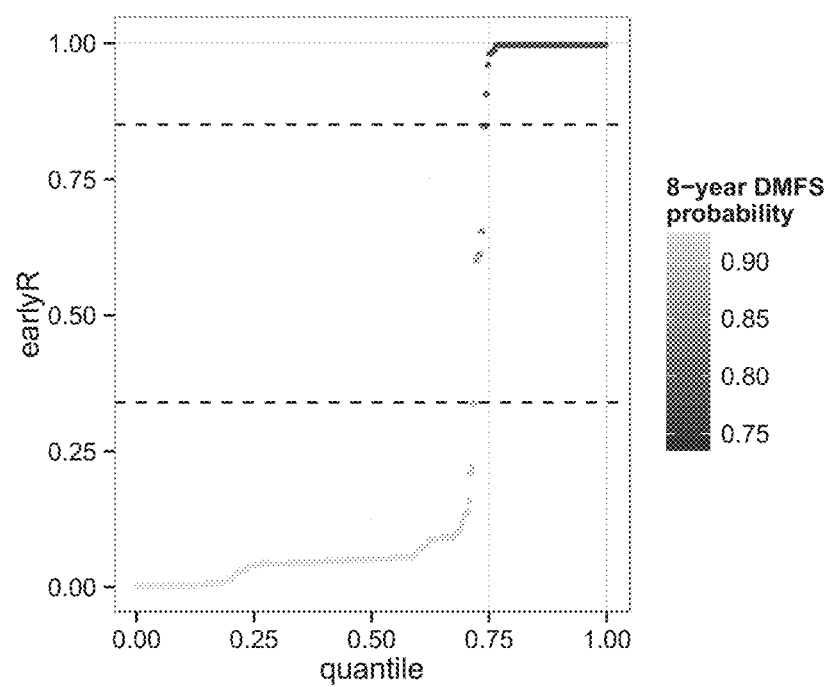
FIG. 14. Plot of the EarlyR score versus the quantiles of the score. The 8-year expected DMFS is indicated in varying shades of gray of the points. The boundaries of the intermediate risk group (dotted lines) are defined by the values of EarlyR at which the expected survival probability is 0.88 and 0.80, specifically, EarlyR=0.34 and EarlyR=0.85, respectively.

In the Affymetrix validation set, EarlyR is significantly prognostic of 8-year DMFS (p=5.1×10−6). Eight-year expected DMFS is very high for low values of EarlyR (<0.25), is very low for EarlyR>0.75, with few samples in between (FIG. 14).

Example 10:—Comparative Observations with Other Screening Tools and Techniques to INDUCT The present invention, employing a patent's individualized INDUCT score, is demonstrated to accurately assess the additive effects of multiple panel genes. The risk score for an individual gene is near 0 (respectively 1) for samples definitively in the low risk (respectively, high risk) component. The INDUCT score is obtained by adding the risk scores for the 5 panel genes and multiplying by 20. Thus, scores of 20, 40, 60, 80, 100 are only exceeded when 1, 2, 3, 4, 5, respectively, panel genes are in the high risk state. Since dividing the population at an INDUCT score of 42 produces a group with long-term relapse-free survival probability >0.92, only samples with more than 2 genes in the high risk state have poor prognosis. This ability of INDUCT to measure the additive effects of panel genes is a major reason for the large good prognosis group it defines.

INDUCT gives a definitive prognosis of low risk or high risk over the entire range of scores. Sets of samples with scores between c and 42, for c<42, have prognosis comparable to the entire good prognosis group, when the set is sufficiently large. Similarly, sets defined with values between 42 and d>42 have very poor prognosis. This behavior contrasts with the Oncotype DX intermediate risk group, which has a moderate prognosis and no clear recommendation for treatment. In one study, the Oncotype DX intermediate risk group contains 40% of the stage I and stage II, and this percentage increased to 66% for the TAILORx intermediate risk group[22].

Commercially available assays for prognostication of patients with ER+ tumors do not outperform traditional (subjective) parameters such as tumor grade. However, they do provide a distinct advantage of being objective in nature [4]. Tang et al [13] reports that the addition of clinical and pathological parameters (tumor grade, size and patient age) to Oncotype DX RS, RSPC, resulted in significant improvement in a multivariate survival model. RSPC significantly improves the Oncotype DX classification by identifying more low risk patients and reducing the number of intermediate risk cases. Similarly, Nielsen et al [14] reports an improvement in the PAM50 score following the addition of clinic-pathological variables. The performance of INDUCT score was therefore evaluated against standard clinical and histopathological features.

The comparison showed that the presently described INDUCT score out performed standard clinic-pathological variables such as patient age, tumor size and tumor grade. More significantly, in LN− samples, the accuracy of prediction and/or prognosis of INDUCT was not improved by adding additional clinic-pathological variables. INDUCT defines a meaningful stratification of patients by risk of relapse across clinico-pathological subgroups of ER+, LN− tamoxifen-treated patients (FIG. 13).

The Metabric dataset includes the PAM50 classifications of the samples, enabling a direct comparison of the prognostic significance of this test and INDUCT. The majority of ER+ samples are classified as Luminal A (good prognosis) or Luminal B (poor prognosis) by PAM50. The low risk and high risk INDUCT subgroups of Luminal A (FIG. 13) have expected survival 0.91 and 0.85, respectively. Most (93%) of the Luminal A samples are INDUCT low risk. On the other hand, low risk and high risk INDUCT subgroups of Luminal B have expected survival 0.93 and 0.81, respectively. The INDUCT low risk group contains 45% of the Luminal B samples. Thus, INDUCT significantly refines the prognosis offered by PAM50. Furthermore, PAM50 offers no meaningful refinement to the INDUCT prognosis.

The analysis of B14 clinical trial using Oncotype DX showed a clear association between RS and benefit from tamoxifen therapy[4]. In particular, Tamoxifen treatment does not lower the risk of relapse in the Oncotype DX high risk group in B14. The benefit from endocrine therapy has since been confirmed in the other trials and is seen both with tamoxifen and aromatase inhibitors. In contrast, INDUCT and Tamoxifen treatment status are independent risk factors in the microarray validation sets. Analysis of INDUCT score showed that INDUCT is significant at the same high level in the patients treated or untreated with tamoxifen (Table 6). Moreover, the hazard ratios of Tamoxifen treatment in the low INDUCT and high INDUCT subgroups of LN− breast cancer are nearly identical.

INDUCT, provides a continuous scale for the assessment of risk of ER+ breast cancer relapse. The present INDUCT screening tool/panel is demonstrated to provide superior performance characteristics as compared to Mammaprint and Oncotype DX RS. In addition, and unlike RS and PAM50, INDUCT is not significantly influenced by addition of clinic-pathological variables such as tumor size or grade, or by use of tamoxifen.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

BIBLIOGRAPHY

The following references are specifically incorporated herein in their entirety.

1. Perou C M, Sorlie T, Eisen M B et al. Molecular portraits of human breast tumours. Nature 2000; 406: 747-752.
2. Wirapati P, Sotiriou C, Kunkel S et al. Meta-analysis of gene expression profiles in breast cancer: toward a unified understanding of breast cancer subtyping and prognosis signatures. Breast Cancer Res 2008; 10: R65.
3. Elston C W, Ellis I O. Pathological prognostic factors in breast cancer. I. The value of histological grade in breast cancer: experience from a large study with long-term follow-up. Histopathology 1991; 19: 403-410.
4. Paik S, Shak S, Tang G et al. A multigene assay to predict recurrence of tamoxifen-treated, node-negative breast cancer. N Engl J Med 2004; 351: 2817-2826.
5. van't Veer L J, Dai H, van de Vijver M J et al. Gene expression profiling predicts clinical outcome of breast cancer. Nature 2002; 415: 530-536.
6. Parker J S, Mullins M, Cheang M C et al. Supervised risk predictor of breast cancer based on intrinsic subtypes. J Clin Oncol 2009; 27: 1160-1167.
7. Dowsett M, Sestak I, Lopez-Knowles E et al. Comparison of PAM50 risk of recurrence score with oncotype DX and IHC4 for predicting risk of distant recurrence after endocrine therapy. J Clin Oncol 2013; 31: 2783-2790.
8. Filipits M, Nielsen T O, Rudas M et al. The PAM50 risk-of-recurrence score predicts risk for late distant recurrence after endocrine therapy in postmenopausal women with endocrine-responsive early breast cancer. Clin Cancer Res 2014; 20: 1298-1305.
9. Gnant M, Filipits M, Greil R et al. Predicting distant recurrence in receptor-positive breast cancer patients with limited clinicopathological risk: using the PAM50 Risk of Recurrence score in 1478 postmenopausal patients of the ABCSG-8 trial treated with adjuvant endocrine therapy alone. Ann Oncol 2014; 25: 339-345.
10. Jorgensen C L, Nielsen T O, Bjerre K D et al. PAM50 breast cancer intrinsic subtypes and effect of gemcitabine in advanced breast cancer patients. Acta Oncol 2014; 53: 776-787.
11. Prat A, Bianchini G, Thomas M et al. Research-based PAM50 subtype predictor identifies higher responses and improved survival outcomes in HER2-positive breast cancer in the NOAH study. Clin Cancer Res 2014; 20: 511-521.
12. Buechler S. Low expression of a few genes indicates good prognosis in estrogen receptor positive breast cancer. BMC Cancer 2009; 9: 243.
13. Tang G, Cuzick J, Costantino J P et al. Risk of recurrence and chemotherapy benefit for patients with node-negative, estrogen receptor-positive breast cancer: recurrence score alone and integrated with pathologic and clinical factors. J Clin Oncol 2011; 29: 4365-4372.
14. Nielsen T O, Parker J S, Leung S et al. A comparison of PAM50 intrinsic subtyping with immunohistochemistry and clinical prognostic factors in tamoxifen-treated estrogen receptor-positive breast cancer. Clin Cancer Res 2010; 16: 5222-5232.
15. Wu Z, Irizarry R A, Gentleman R et al. A Model-Based Background Adjustment for Oligonucleotide Expression Arrays. Journal of the American Statistical Association 2004; 99: 909-917.
16. Curtis C, Shah S P, Chin S F et al. The genomic and transcriptomic architecture of 2,000 breast tumours reveals novel subgroups. Nature 2012; 486: 346-352.
17. Fraley C, Raftery A E. Model-based clustering, discriminant analysis, and density estimation J Amer Statist Assn 2002; 97: 611-631.

18. Fraley C, Raftery A E. mclust version 4 for R: normal mixture modeling for model-based clustering, classification, and density estimation. Technical Report No. 597 2012; Department of Statistics, University of Washington.
19. Gray R J. Flexible methods for analyzing survival data using splines, with applications to breast cancer prognosis. J Amer Statist Assn 1992; 87: 942-951.
20. Paik S, Shak S, Tang G et al. Expression of the 21 genes in the Recurrence Score assay and tamoxifen clinical benefit in the NSABP study B-14 of node negative, estrogen receptor positive breast cancer Proc ASCO 2005; 23: 510.
21. Sotiriou C, Wirapati P, Loi S et al. Gene expression profiling in breast cancer: understanding the molecular basis of histologic grade to improve prognosis. J Natl Cancer Inst 2006; 98: 262-272.
22. Kelly C M, Bernard P S, Krishnamurthy S et al. Agreement in risk prediction between the 21-gene recurrence score assay (Oncotype DX®) and the PAM50 breast cancer intrinsic Classifier in early-stage estrogen receptor-positive breast cancer. Oncologist 2012; 17: 492-498.

The invention claimed is:

1. A kit comprising:
a set of nucleic acid probes, wherein the set of nucleic acid probes consists of single-stranded polynucleotides complementary to mRNA or cDNA, wherein within the set of probes each probe is complementary to the cDNA or mRNA of a gene selected from the group consisting of: MK167, SPAG5, ESPL1, PLK1 and PGR, wherein the set of probes includes a probe for each of the genes, wherein the nucleic acid probes are covalently attached to a solid substrate.

2. The kit of claim 1 wherein the kit is compatible with automated nucleic acid detection techniques.

3. The kit of claim 1 further comprising a control or reference sample.

4. The kit of claim 1 further comprising an instructional insert.

5. The kit of claim 1 wherein the nucleic acid probes are labeled.

* * * * *